(12) United States Patent
Dejana et al.

(10) Patent No.: US 12,377,092 B2
(45) Date of Patent: Aug. 5, 2025

(54) POLYCOMB INHIBITORS AND USES THEREOF

(71) Applicant: FONDAZIONE ISTITUTO FIRC DI ONCOLOGIA MOLECOLARE (IFOM), Milan (IT)

(72) Inventors: Elisabetta Dejana, Milan (IT); Matteo Malinverno, Milan (IT)

(73) Assignee: FONDAZIONE ISTITUTO FIRC DI ONCOLOGIA MOLECOLARE (IFOM), Milan (IT)

( * ) Notice: Subject to any disclaimer, the term of this patent is extended or adjusted under 35 U.S.C. 154(b) by 662 days.

(21) Appl. No.: 16/768,234

(22) PCT Filed: Dec. 10, 2018

(86) PCT No.: PCT/EP2018/084216
§ 371 (c)(1),
(2) Date: May 29, 2020

(87) PCT Pub. No.: WO2019/115472
PCT Pub. Date: Jun. 20, 2019

(65) Prior Publication Data
US 2021/0205300 A1    Jul. 8, 2021

(30) Foreign Application Priority Data

Dec. 11, 2017 (EP) .................... 17206417

(51) Int. Cl.
| | | |
|---|---|---|
| A61K 31/496 | (2006.01) | |
| A61K 31/519 | (2006.01) | |
| A61K 45/06 | (2006.01) | |

(52) U.S. Cl.
CPC .......... *A61K 31/496* (2013.01); *A61K 31/519* (2013.01); *A61K 45/06* (2013.01)

(58) Field of Classification Search
CPC ..... A61K 31/496; A61K 31/519; A61K 45/06
See application file for complete search history.

(56) References Cited

U.S. PATENT DOCUMENTS

2019/0151274 A1* 5/2019 Seyfried ................ A61K 31/07

FOREIGN PATENT DOCUMENTS

| WO | 2015120372 A2 | 8/2015 | |
|---|---|---|---|
| WO | 2017070194 A1 | 4/2017 | |
| WO | WO-2018025098 A1 * | 2/2018 | ........... C12N 15/113 |

OTHER PUBLICATIONS

Hong, et al., Euro. J. Cell Bio., 97:493. (Year: 2018).*
Madar, et al., Trends in Molecular Medicine, 19:447. (Year: 2013).*
Gasparics, et al., Am. J. Physiol. Heart Circ. Physiol., 310:H1055. (Year: 2016).*
Karasek, M., Medical Hypotheses, 68:650 (Year: 2007).*
Piera-Velazquez, et al., J. Clin. Med., 5:45 (Year: 2016).*
Mahler, et al., Biotech. And Bioeng., 111:2326. (Year: 2014).*
Arciniegas, et al., Am. J. Phsiol. Lung Cell Mol. Physiol., 293:L1. (Year: 2007).*
Evrard, et al., Nat. Commun., 7:11853. (Year: 2016).*
Boström, et al., Atherosclerosis, 253:124. (Year: 2016).*
Cao, e al., IOVS, 55:7321. (Year: 2014).*
Bravi, et al., Stroke, 47:886. (Year: 2016).*
Ramirez, et al., Histol. Histopathol., 29:1281. (Year: 2014).*
Rizq, et al., Clin. Cancer Res., 23:4817. (Year: 2017).*
Yu et al., "The EZH2 inhibitor GSK343 suppresses cancer stem-like phenotypes and reverses mesenchymal transition in glioma cells", Oncotarget, 2017, vol. 8, No. 58, pp. 98348-98359.
Zhang et al., "Enhancer of Zeste homolog 2 (EZH2) induces epithelial-mesenchymal transition in endometriosis", Scientific Reports, 2017, vol. 7, No. 1, pp. 1-12.
Liu et al., "Downregulation of Bmi-1 suppresses epithelial-mesenchymal transition in melanoma", Oncology Reports, 2016, vol. 37, No. 1, pp. 139-146.
Mayr et al.,"The BMI1 inhibitor PTC-209 is a potential compound to halt cellular growth in biliary tract cancer cells", Oncotarget,2016, vol. 7, No. 1, pp. 745-758.
Maddaluno et al., "EndMT contributes to the onset and progression of cerebral cavernous malformations", Nature, 2013, vol. 498, No. 7455, pp. 492-496.
Konze et al., "An Orally Bioavailable Chemical Probe of the Lysine Methyltransferases EZH2 and EZH1", ACS Chemical Biology, 2013, vol. 8, No. 6, pp. 1324-1334.
Ruiz et al., "Polycomb Repressive Complex 2 Regulates MIR-200b in Retinal Endothelial Cells: Potential Relevance in Diabetic Retinopathy", PLOS One, 2015, vol. 10, No. 4, pp. 1-22.
International Search Report and Written Opinion for Corresponding International Application No. PCT/EP2018/084216 (15 Pages) (Feb. 15, 2019).

* cited by examiner

*Primary Examiner* — Joseph K McKane
*Assistant Examiner* — Quincy McKoy
(74) *Attorney, Agent, or Firm* — Lucas & Mercanti, LLP

(57) ABSTRACT

An inhibitor of polycomb for use in the treatment and/or prevention of an endothelial to mesenchymal transition associated pathology is provided. Preferably, the inhibitor inhibits at least one polycomb repressive complex. The present invention also relates to a pharmaceutical composition having an inhibitor of polycomb for use in the treatment and/or prevention of an endothelial to mesenchymal transition associated pathology and to a method to identify an inhibitor of polycomb.

13 Claims, 19 Drawing Sheets

Specification includes a Sequence Listing.

(Vleminckx, Kemler, & Hecht, 1999)

Source: Margueron & Reinberg, Nature 469, 343-349

SEQUENCE LISTING

```
<160> NUMBER OF SEQ ID NOS: 7

<210> SEQ ID NO 1
<211> LENGTH: 23
<212> TYPE: DNA
<213> ORGANISM: Artificial Sequence
<220> FEATURE:
<223> OTHER INFORMATION: synthetic primer

<400> SEQUENCE: 1
cacttgtcta ataccaacaa ggg                                           23

<210> SEQ ID NO 2
<211> LENGTH: 22
<212> TYPE: DNA
<213> ORGANISM: Artificial Sequence
<220> FEATURE:
<223> OTHER INFORMATION: synthetic primer

<400> SEQUENCE: 2
cctatctaca tctccctatt gc                                            22
```

```
<210> SEQ ID NO 3
<211> LENGTH: 24
<212> TYPE: DNA
<213> ORGANISM: Artificial Sequence
<220> FEATURE:
<223> OTHER INFORMATION: synthetic primer

<400> SEQUENCE: 3
gataggaatt attactgccc ttcc                                            24

<210> SEQ ID NO 4
<211> LENGTH: 21
<212> TYPE: DNA
<213> ORGANISM: Artificial Sequence
<220> FEATURE:
<223> OTHER INFORMATION: synthetic primer

<400> SEQUENCE: 4
gacaagaaag cactgttgac c                                               21

<210> SEQ ID NO 5
<211> LENGTH: 23
<212> TYPE: DNA
<213> ORGANISM: Artificial Sequence
<220> FEATURE:
<223> OTHER INFORMATION: synthetic primer

<400> SEQUENCE: 5
gaattaattc cggtataact tcg                                             23

<210> SEQ ID NO 6
<211> LENGTH: 21
<212> TYPE: DNA
<213> ORGANISM: Artificial Sequence
<220> FEATURE:
<223> OTHER INFORMATION: synthetic primer

<400> SEQUENCE: 6
aaagtcgctc tgagttgtta t                                               21

<210> SEQ ID NO 7
<211> LENGTH: 20
<212> TYPE: DNA
<213> ORGANISM: Artificial Sequence
<220> FEATURE:
<223> OTHER INFORMATION: synthetic primer

<400> SEQUENCE: 7
ccagatgact acctatcctc                                                 20
```

POLYCOMB INHIBITORS AND USES THEREOF

CROSS-REFERENCE TO RELATED APPLICATIONS

This application is a 371 of PCT/EP2018/084216, filed Dec. 10, 2018, which claims the benefit of European Patent Application No. 17206417.2, filed Dec. 11, 2017.

TECHNICAL FIELD

The present invention refers to an inhibitor of polycomb for use in the treatment and/or prevention of an endothelial to mesenchymal transition associated pathology, preferably the inhibitor inhibits at least one polycomb repressive complex. The present invention also relates to a pharmaceutical composition comprising said inhibitor of polycomb for use in the treatment and/or prevention of an endothelial to mesenchymal transition associated pathology and to a method to identify an inhibitor of polycomb.

BACKGROUND ART

Cerebral Cavernous Malformations (CCM) is a rare genetic disease characterized by capillary-venous malformations, mostly located in the central nervous system that may cause micro bleeds leading to epileptic seizures and cerebral hemorrhages.

The disease occurs as sporadic and familial form. The familial form has an overall prevalence of <1/10,000 and is characterized by the presence of multiple CCM lesions that increase in number and size during patients' life and cause recurrent cerebral hemorrhages. Familial C C M is due to loss of function mutations in any one of three genes called Ccm1 (or Krit1), Ccm2 (Osm) and Ccm3 (or PDCD10). These genes encode three cytoplasmic proteins that, besides other specific functions, form a tripartite complex associated to endothelial cell (EC) junctions that increases junction strength and maintains endothelial homeostasis. Remarkably, the morphology and specific brain localization is comparable in the three types of CCM loss of function mutations. The sporadic form of CCM has a relatively high prevalence (1/100-200 individuals) and, in the majority of the cases, occurs as a single cavernoma. However, depending on the location of the cavernoma also this form may cause a quite variable set of symptoms such as seizures, headache, paralysis and, eventually, hemorrhagic stroke.

Effective medical treatment that may limit disease progression is dearly needed, as available curative therapy is limited to surgical lesion eradication or stereotactic radio-surgery. Open skull surgery is currently applied to selected symptomatic lesions only (after hemorrhage or symptomatic lesion growth), but it is highly invasive with at times significant complications and unproven long-term benefit. Despite many research efforts, an effective medical therapy for this disease and for endothelial to mesenchymal transition associated pathologies for is still missing.

The detailed knowledge of the signaling pathways that induce the functional and morphological alteration of the vessels is a prerequisite for the definition of a pharmacological intervention.

The inventors showed, in mouse models as well as in human patients, that the ECs lining the cavernomas present different features than the surrounding ECs of the same vessel. Specifically, ECs show a mixed phenotype combining both endothelial and mesenchymal/stem cell features in a way similar to the so-called endothelial-to-mesenchymal transition (EndMT). These characteristics combined to high proliferation and loss of the normal architecture of the vascular lesions are reminiscent of tumor initiating cells that undergo epithelial-to-mesenchymal transition, loose polarity and contact inhibition of cell growth.

Interestingly, the endothelial-to-mesenchymal transition plays a crucial role in different pathology beside CCM. In particular, EndMT has been described in atherosclerosis, transplant arteriopathy, cardiac fibrosis, chronic obstructive pulmonary disease (COPD), pulmonary fibrosis, portal hypertension, heterotopic ossification systemic sclerosis, diabetic renal interstitial fibrosis, primary mielofibrosis, fibrotic disorders and others (Dejana et al. Nat comm 2016).

Polycomb group of proteins are a family of evolutionary conserved chromatin repressors that play an essential role in maintaining the correct identities of stem, progenitor and differentiated cells[34-37]. Their functional role is strictly cell context dependent and they have been widely studied in different types of cancer. The polycomb complex PRC2 is formed by a trimeric core of Suz12, EeD and EZH1/2 (chromatin modifier enhancer of zeste homolog 2) and catalyses methylation of Histone H3 at lysine 27. The polycomb complex PRC1 presents a much higher complexity and is required for histone H2AK119 ubiquitination via E3 ligases Ring1a and Ring 1b. PRC1 mono-ubiquitinates histone H2A on lysine 119 (H2AK119Ub1). In general, the polycomb group of proteins exert a control on process of cell proliferation and establishment of cellular identity.

SUMMARY OF THE INVENTION

In the present invention by testing potential chemical inhibitors of End-MT induced by the abrogation of CCM, the inventors surprisingly found that at least two inhibitors of the chromatin regulators Polycombs were strongly effective. The capacity of Polycomb inhibitors to abrogate End-MT markers and induce maturation of CCM deficient endothelial cells make them particularly suitable for therapeutic use.

More specifically, in the present invention the inventors showed that at least three chemical inhibitors have shown clinical responses in cancer patients and were also able to abrogate the expression of End-MT markers in vitro and to inhibit the formation of the cavernomas in animal models. The three inhibitors are PRC2 (UNC1999, which inhibits both Ezh1 and Ezh2),[38,39] PRC1 (PTC-209, which inhibits BMI-1)[40] and PTC-596.

PRC1, PTC-209 is known as N-(2,6-dibromo-4-methoxyphenyl)-4-(2-methylimidazo[1,2-a]pyrimidin-3-yl)thiazol-2-amine and has the chemical structure:

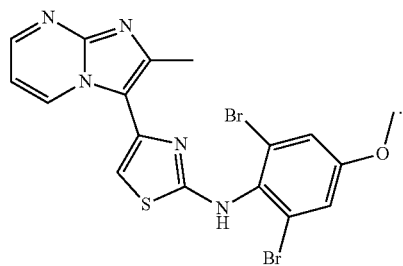 [SMILES: COc1cc(Br)c(Nc2nc(-c3c(C)nc4ncccn34)cs2)c(Br)c1]

PRC2, UNC1999 is known as N-[(6-methyl-2-oxo-4-propyl-1H-pyridin-3-yl)methyl]-1-propan-2-yl-6-[6-(4-propan-2-ylpiperazin-1-yl) pyridin-3-yl]indazole-4-carboxamide and has the chemical structure:

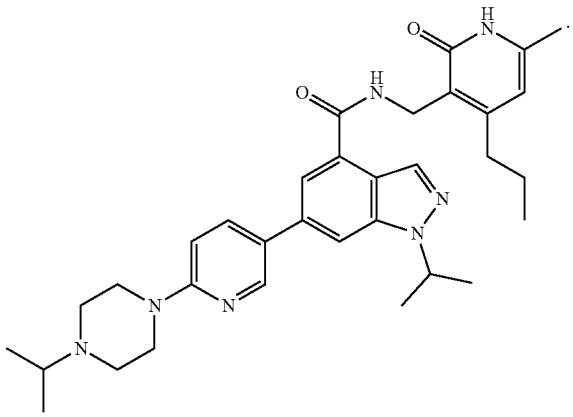 [SMILES: CCCc1cc(C)[nH]c(=O)c1CNC(=O)c1cc(-c2ccc(N3CCN(C(C)C)CC3)nc2)cc2c1cnn2C(C)C]

PTC-596 is known as 5-fluoro-2-(6-fluoro-2-methyl-1H-benzold|imidazol-1-yl)-N4-(4-(trifluoromethyl)phenyl)pyrimidine-4,6-diamine hydrochloride and has the chemical structure:

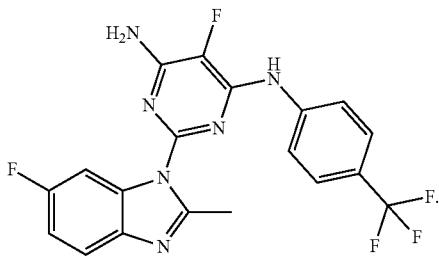 [SMILES: Cc1nc2ccc(F)cc2n1-c1nc(N)c(F)c(Nc2ccc(C(F)(F)F)cc2)n1]

Thus, inhibitors of PRC1 and PRC2 represent a valid therapeutic strategy to inhibit EndMT and therefore treat all the pathological condition associated to EndMT.

Therefore, the invention provides an inhibitor of polycomb for use in the treatment and/or prevention of an endothelial to mesenchymal transition associated pathology.

The invention provides a method of treatment of an endothelial to mesenchymal transition associated pathology comprising administering to a subject in need thereof a therapeutically effective amount of an inhibitor of polycomb.

The invention also provides the use of an inhibitor of polycomb for the manufacture of a medicament for the treatment and/or prevention of an endothelial to mesenchymal transition associated pathology.

The inhibitor may be a small molecule, a protein, peptide, antisense nucleic acid, an antibody or any agent that inhibits polycomb.

Preferably said inhibitor is an inhibitor of at least one polycomb Repressive Complex.

Preferably the polycomb Repressive Complex is PRC1 or PRC2.

Preferably said inhibitor is an inhibitor of Bmi1 or an inhibitor of Ezh2 and/or Ezh1. Preferably the inhibitor of Bmi1 is PTC-209 or a derivative or analog thereof or a pharmaceutically acceptable salt thereof and the inhibitor of Ezh2 and/or Ezh1 is UNC1999 or a derivative or analog thereof or a pharmaceutically acceptable salt thereof.

Preferably said inhibitor is used in combination with at least a further therapeutic agent.

Preferably the further therapeutic agent is selected from the group consisting of: an inhibitor of polycomb, an inhibitor of β-catenin (such as silibinin, curcumin, resveratrol, salinomycin, propranolol), anti-oxidant, TGF-β signaling pathway inhibitors, BMP signaling pathway inhibitors, VEGF signaling pathway inhibitors, Yap signaling pathway inhibitors, statins and inhibitors of RhoA GTPase levels and/or activity.

Preferably the further agent is another inhibitor of polycomb.

A preferred embodiment is the combination of PTC-209 and UNC1999 or a pharmaceutically acceptable salt thereof.

The invention also provides a pharmaceutical composition comprising at least one inhibitor of polycomb as defined above for use in the treatment and/or prevention of an endothelial to mesenchymal transition associated pathology.

Preferably the pharmaceutical composition comprises at least a further therapeutic agent.

Preferably the further therapeutic agent is selected from the group consisting of: an inhibitor of polycomb, an inhibitor of b-catenin (such as silibinin, curcumin, resveratrol, salinomycin, propranolol), anti-oxidant, TGF-β signaling pathway inhibitors, BMP signaling pathway inhibitors, VEGF signaling pathway inhibitors, Yap signaling pathway inhibitors, statins and inhibitors of RhoA GTPase levels and/or activity.

Preferably the pharmaceutical composition comprises a combination of PTC-209 and UNC1999 or a pharmaceutically acceptable salt thereof.

Preferably the endothelial to mesenchymal transition associated pathology is selected from the group consisting of: Cerebral Cavernous Malformation, atherosclerosis, transplant arteriopathy, cardiac fibrosis, chronic obstructive pulmonary disease (COPD), pulmonary fibrosis, portal hypertension, heterotopic ossification systemic sclerosis, diabetic renal interstitial fibrosis, diabetes retinopathy, primary mielofibrosis, fibrodysplasia ossificans progressiva, kidney fibrosis.

Preferably the cerebral cavernous malformation is sporadic or familial.

Preferably the cerebral cavernous malformation is caused by a mutation in at least one gene selected from CCM1, CCM2 or CCM3.

The present invention also provides a method for identifying a polycomb inhibitor, said method comprising measuring the expression level of H2AK119Ub1 and/or measuring the monoubiquitylation of histone H2A and/or measuring the E3 ligase activity and/or measuring the expression level of Bmi1 and/or the catalytic activity of Bmi1 and/or measuring the expression level of p16$^{Ink4a}$ and/or p19$^{Arf}$ and/or measuring the expression level of H3K27m3 and/or measuring the catalytic activity of Ezh1 and/or Ezh2 and comparing said measured expression level and/or said measured activity to a proper control expression level or activity. Said measurements may be performed by western-blot on cell and/or tissues lysates and/or immuno-fluorescence on cells and/or tissue samples and/or immuno-histochemistry on tissue samples or any known methods in the art.

An inhibitor of polycomb is any agent that inhibits at least one protein of the polycomb group as defined below. For example, the inhibitor may inhibit at least one polycomb protein activity directly or indirectly by a) acting on polycomb, b) by interfering with the expression of polycomb, c) acting on any element of polycomb repressive complexes as shown in FIG. 31. In particular, member of the complex are Ring1a/b, Mel18, Bmi1 and PCGF1-6 for the PRC1 and Ezh1/2, Suz12, EED and RbAp48 for the PRC2.

The inhibitor may act on transcription and/or post-translation activities of at least one protein of the polycomb group.

In the present invention polycomb Group (PcG) proteins are a family of epigenetic regulators of transcription that catalyse H3K27me3 and H2AK119Ub1. PcG proteins were first discovered as epigenetic repressors of homeotic gene (Hox) expression in *Drosophila melanogaster*, which allows them to control anterior-posterior segment identity, differentiation and body planning (Bunker & Kingston, 1994). More recently, the role of PcG proteins in human carcinogenesis and cancer progression has been demonstrated: their deregulation or dysfunction leads to inappropriate activation of developmental pathways increasing proliferation, inhibiting apoptosis and increasing cancer cells population. Thus, they can act directly on several oncogenes and tumor suppressor genes.

Moreover, PcG proteins target transcription factors, signalling proteins, morphogens and regulators involved in all major developmental pathways.

Polycomb Repressive Complexes (PRCs) comprise PRC1 and PRC2, both involved in histone modifications. Biochemically PRC1 employs an E3 ligase (RING1A or RING1B) to induce H2AK119Ub1 while PRC2 catalyse H3K27me3.

PRC1 is a complex of proteins that has a ubiquitin Ring Finger E3 ligase and catalyses the monoubiquitylation of histone H2A. It is composed of several subunits: the chromodomain protein family (CBX2, CBX4, CBX6, CBX7 and CBX8), the mammalian homologs of Ph PH1, PH2, and PH3, the homologs of dRing named RING1A and RING1B and finally, BMI1, NSPC1, MEL18, PCGF3, PCGF5 and MBLR, which collectively are named the PcG RING fingers (PCGFs).

A typical assay for PRC1 activity is to evaluate the level of H2AK119Ub1 according to standard method known in the art such as western-blot on cell and/or tissues lysates and/or immunofluorescence on cells and/or tissue samples and/or immunohistochemistry on tissue samples.

A PRC1 inhibitor is any compound able to inhibit the monoubiquitylation of histone H2A. PRC1 inhibitors can inhibit either the expression of anyone of its subunits (the chromodomain protein family (CBX2, CBX4, CBX6, CBX7 and CBX8), the mammalian homologs of Ph PH1, PH2, and PH3, the homologs of dRing named RING1A and RING1B and BMI1, NSPC1, MEL18, PCGF3, PCGF5 and MBLR, collectively named the PcG RING fingers (PCGFs)), or the E3 ligase activity.

An inhibitor of Prc1 may be for example 1) PRT 4165, an inhibitor of Ring1 Ubiquitin Ligase (E3) activity (Ismail I H et al. 2013) or 2) PTC-209 (Kreso et al. Nature Med 2013) and PTC-596 (Nishida et al. 2017), inhibitors of Bmi1.

An inhibitor of Bmi1 is any compound able to inhibit 1) the expression of Bmi1, 2) the catalytic activity of Bmi1 (the ubiquitination of Histone 2A), or 3) the combination of the two. Direct target genes of Bmi1 are p16$^{Ink4a}$ and p19$^{Arf}$, which are repressed by Bmi1 activity. Thus, Bmi1 inhibition can be measured by measuring: 1) expression level of Bmi1, 2) expression of H2AK119Ub1 or 3) expression of p16$^{Ink4a}$ and p19$^{Arf}$.

The level of expression of Bmi1, H2AK119Ub1 or p16$^{Ink4a}$ and p19$^{Arf}$ may be measured according to standard method known in the art such as western-blot on cell and/or tissues lysates and/or immunofluorescence on cells and/or tissue samples and/or immunohistochemistry on tissue samples and/or quantitative RT-qPCR.

A Bmi1 inhibitor may be for example: PTC-209, PTC-596.

PRC2 is composed of the following proteins: EZH1/2, EeD, SUZ12, RbBP4, AEBP2, Jarid2, Pcl1; where the catalytic subunits are Ezh1 or Ezh2. Despite the compositions, the final effect of PRC2 activity is the tri-methylation of lysine 27 of histone H3 (H3K27m3). Thus, a typical assay for PRC2 activity is to evaluate the level of H3K27m3 according to standard method known in the art such as western-blot on cell and/or tissues lysates and/or immunofluorescence on cells and/or tissue samples and/or immunohistochemistry on tissue samples.

An inhibitor of PRC2 can inhibit either the expression of anyone of its components, or the catalytic activity of Ezh1 and/or Ezh2.

An inhibitor of the catalytic subunit Ezh1/2 may be for example as described in the following articles, all incorporated by reference: Clin Cancer Res. 2012 Jan. 1; 18 (1): 77-90. doi: 10.1158/1078-0432.CCR-11-0962. Epub 2011 Oct. 25. Polycomb repressor complex-2 is a novel target for mesothelioma therapy; Kemp C D, Rao M, Xi S, Inchauste S, Mani H, Fetsch P, Filie A, Zhang M, Hong J A, Walker R L, Zhu Y J, Ripley R T, Mathur A, Liu F, Yang M, Meltzer P A, Marquez V E, De Rienzo A, Bueno R, Schrump D S. Cancer Res. 2009 Dec. 15; 69 (24): 9211-8. doi: 10.1158/0008-5472.CAN-09-1622. EZH2 is essential for glioblastoma cancer stem cell maintenance; Suvà ML, Riggi N, Janiszewska M, Radovanovic I, Provero P, Stehle J C, Baumer K, Le Bitoux M A, Marino D, Cironi L, Marquez V E, Clément V, Stamenkovic I. Breast Cancer Res Treat. 2011 May; 127 (1): 109-19. doi: 10.1007/s10549-010-0982-0. Epub 2010 Jun. 17. S-adenosylhomocysteine hydrolase inhibition by 3-deazaneplanocin A analogues induces anti-cancer effects in breast cancer cell lines and synergy with both histone deacetylase and HER2 inhibition; Hayden A, Johnson P W, Packham G, Crabb S J. PLOS One. 2011 Jan. 28; 6 (1): e16282. doi: 10.1371/journal.pone.0016282. Downregulation of miR-101 in endothelial cells promotes blood vessel formation through reduced repression of EZH2; Smits M, Mir S E, Nilsson R J, van der Stoop P M, Niers J M, Marquez V E, Cloos J, Breakefield X O, Krichevsky A M, Noske D P, Tannous B A, Würdinger T. Proc Natl Acad Sci USA. 2012 Dec. 26; 109 (52): 21360-5. doi: 10.1073/pnas.1210371110. Epub 2012 Dec. 10. Selective inhibition of Ezh2 by a small molecule inhibitor blocks tumor cells proliferation; Qi W, Chan H, Teng L, Li L, Chuai S, Zhang R, Zeng J, Li M, Fan H, Lin Y, Gu J, Ardayfio O, Zhang J H, Yan X, Fang J, Mi Y, Zhang M, Zhou T, Feng G, Chen Z, Li G, Yang T, Zhao K, Liu X, Yu Z, Lu C X, Atadja P, Li E. Nat Chem Biol. 2012 November; 8 (11): 890-6. doi: 10.1038/nchembio.1084. Epub 2012 Sep. 30. A selective inhibitor of EZH2 blocks H3K27 methylation and kills mutant lymphoma cells; Knutson S K, Wigle T J, Warholic N M, Sneeringer C J, Allain C J, Klaus C R, Sacks J D, Raimondi A, Majer C R, Song J, Scott M P, Jin L, Smith J J, Olhava E J, Chesworth R, Moyer M P, Richon V M, Copeland R A, Keilhack H, Pollock R M, Kuntz K W. Mol Cancer Ther. 2014 April; 13 (4): 842-54. doi: 10.1158/1535-7163.MCT-13-0773. Epub 2014 Feb. 21. Selective inhibition of EZH2 by EPZ-6438 leads to potent antitumor activity in EZH2-mutant non-Hodgkin lymphoma; Knutson S K, Kawano S, Minoshima Y, Warholic N M, Huang K C, Xiao Y, Kadowaki T, Uesugi M, Kuznetsov G, Kumar N, Wigle T J, Klaus C R, Allain C J, Raimondi A, Waters N J, Smith J J, Porter-Scott M, Chesworth R, Moyer M P, Copeland R A, Richon V M, Uenaka T, Pollock R M, Kuntz K W, Yokoi A, Keilhack H. Proc Natl Acad Sci USA. 2013 May 7; 110 (19): 7922-7. doi: 10.1073/pnas.1303800110. Epub 2013 Apr. 25. Durable tumor regression in genetically altered malignant rhabdoid tumors by inhibition of methyltransferase EZH2; Knutson S K, Warholic N M, Wigle T J, Klaus C R, Allain C J, Raimondi A, Porter Scott M, Chesworth R, Moyer M P, Copeland R A, Richon V M, Pollock R M, Kuntz K W, Keilhack H. ACS Med Chem Lett. 2012 Oct. 19; 3 (12): 1091-6. doi: 10.1021/ml3003346. eCollection 2012 Dec. 13. Identification of Potent, Selective, Cell-Active Inhibitors of the Histone Lysine Methyltransferase EZH2; Verma SK1, Tian X, LaFrance L V, Duquenne C, Suarez D P, Newlander K A, Romeril S P, Burgess J L, Grant S W, Brackley J A, Graves A P, Scherzer D A, Shu A, Thompson C, Ott H M, Aller G S, Machutta C A, Diaz E, Jiang Y, Johnson N W, Knight S D, Kruger R G, McCabe M T, Dhanak D, Tummino P J, Creasy C L, Miller W H, Nature. 2012 Dec. 6; 492 (7427): 108-12. doi: 10.1038/nature11606. Epub 2012 Oct. 10. EZH2 inhibition as a therapeutic strategy for lymphoma with EZH2-activating mutations; McCabe M T, Ott H M, Ganji G, Korenchuk S, Thompson C, Van Aller G S, Liu Y, Graves A P, Della Pietra A 3rd, Diaz E, LaFrance L V, Mellinger M, Duquenne C, Tian X, Kruger R G, McHugh C F, Brandt M, Miller W H, Dhanak D, Verma S K, Tummino P J, Creasy C L. Nat Chem Biol. 2013 October; 9 (10): 643-50. doi: 10.1038/nchembio.1331. Epub 2013 Aug. 25. Targeted disruption of the EZH2-EED complex inhibits EZH2-dependent cancer; Kim W, Bird G H, Neff T, Guo G, Kerenyi M A, Walensky L D, Orkin S H.

DZNep (Hayden et al., Breast Cancer Res Treat. 2011 May; 127 (1): 109-19; Kemp et al., Clin Cancer Res. 2012 Jan. 1; 18 (1): 77-90; Suvà et al. Cancer Res. 2009 Dec. 15; 69 (24): 9211-8.; Smits et al., PLOS One. 2011 Jan. 28; 6 (1): e16282.), EI1 (Qi, W. et al. PNAS 2012 Dec. 26; 109 (52): 21360-5.), EPZ005687. (Knutson, S. K. et al. Nat Chem Biol. 2012 November; 8 (11): 890-6.), GSK343 (Verma, S. K. et al., ACS Med Chem Lett. 2012 Oct. 19; 3 (12): 1091-6), GSK126 or GSK2816126 (McCabe et al. Nature. 2012 Dec. 6; 492 (7427): 108-12.), UNC1999 (Konze et al. 2013) which is a dual EZH1/2 inhibitor, EPZ-6438 (knutson, S. K. et al. PNAS 2013 May 7; 110 (19): 7922-7; knutson, S. K. et al. Mol Cancer Ther. 2014 April; 13 (4): 842-54), Stabilized α-helix of EZH2 peptide (SAH-EZH2, Kim, W. et al. Nat Chem Biol. 2013 October; 9 (10): 643-50) which is a EZH2 inhibitor disrupting EZH2/EED complex, CPI-169 (Bradley W D et al., Chemistry and biology 21, 1463-1475, 2014), JQEZ-5 (Souroullas G. P et a., Nat Med 22 (6): 632-640, 2016), KM-301 (Kainos medicine) and ORS-1 (Daiichi Sankyo Co Ltd).

An endothelial to mesenchymal transition (EndMT) associated pathology is any pathological condition in which endothelial cells undergo endothelial-to-mesenchymal transition, and this transition plays a crucial role in the onset and progression of the pathology (Dejana et al, Nat Comm 2017).

The references Ismail I H et al. 2013, Kreso et al. Nature Med 2013, Nishida et al. 2017, Hayden et al. 2011; Kemp et al. 2012; Suvà et al. 2009; Smits et al. 2011, Qi, W. et al. 2012, Knutson, S. K. et al. 2012, Verma, S. K. et al. 2012, McCabe et al. 2012, Konze et al. 2013, knutson, S. K. et al. 2013; knutson, S. K. et al. 2014, Kim, W. et al. 2013, Bradley W D et al., Souroullas G. P et al., Nat Med 22 (6): 632-640, 2016) are all incorporated by reference. Any inhibitor described therein is part of the present invention.

In the context of the present invention, a "derivative" or "analog" of a polycomb inhibitor includes a chemical modification made for the purpose of improving its properties, especially its pharmacokinetic, pharmacodynamic, chemical or physical properties. For example, a derivative may be a chemical modification made to the inhibitor for the purpose of increasing its half-life.

As intended herein, the terms "inhibit" or "decrease" encompass a measurable reduction by at least 20%, 50%, 70%, 75%, or 80% over untreated controls.

There is also provided a method of treating an endothelial to mesenchymal transition associated pathology comprising administering a therapeutically effective amount of an inhibitor of polycomb of the present invention to a subject in need thereof.

A therapeutically effective amount of an inhibitor of the invention will suitably be approximately 600 mg and may be administered between twice a week and once per month (however these doses and frequencies are purely illustrative and non-limiting). More generally, a dose of 0.001 to 200 mg/kg, for instance 0.2-100 mg/kg, preferably 0.2-50 mg/kg, preferably 0.2-20 mg/kg, preferably 0.2-10 mg/kg, preferably 0.2-7 mg/kg, preferably 0.2-5 mg/kg may be suitable.

Compositions

The invention provides an inhibitor of the invention together with one or more pharmaceutically acceptable diluents or carriers. A composition, e.g. for injection, will suitably comprise the inhibitor of the invention together with water for injection and appropriate buffering salts (e.g. citrate, Tris, phosphate salts) and substances (e.g. salts or polyols) to modify the tonicity of the composition. The pH of an aqueous composition may be adjusted for optimal protein stability or physiological comfort and may, for example, be around 6.5 to 8.5 e.g. 7-7.4. Other possible composition components include complexing agents (e.g. EDTA), anti-oxidants and preservatives. A composition of the invention may be provided in lyophilised form suitable for reconstitution with water for injection. Lyophilised compositions may contain bulking agents such as mannitol and lyoprotectants such as polyols e.g. trehalose or sucrose. As well as by the parenteral route, the inhibitor may also be administered by other routes, for example intranasally, by inhalation or by epicutaneous administration. Exemplary compositions may be gleaned by reference to Remington's Pharmaceutical Sciences (18th Ed, A R Gennaro, ed, Mack Publishing Company, 1990).

Combinations

The inhibitor of the invention may be administered in combination with other active ingredients. The inhibitor of the invention might be administered in association with anticonvulsant, anti-inflammatory drugs for the treatment and prevention of an endothelial to mesenchymal transition associated pathology.

Such combinations may be administered separately or simultaneously and may be administered in the same composition or in different compositions and may be administered by the same route or different routes.

In a preferred embodiment the other therapeutic agent is selected from the group of: anti-oxidant, TGF-β signaling pathway inhibitors, BMP signaling pathway inhibitors, VEGF signaling pathway inhibitors, Yap signaling pathway inhibitors, statins (see for example Hwang et al, 2013, Int J. Oncol 43, 261-270) and inhibitors of RhoA GTPase levels and/or activity.

In a preferred embodiment the pharmaceutical acceptable vehicle is a nanoparticle, preferably the nanoparticle is engineered to target pathological endothelial cells.

According to this aspect of the invention, a treatment and/or prevention of an endothelial to mesenchymal transition associated pathology can be effective to mitigate at least one symptom of said pathology.

When treating the underlying cause of the pathology, it is believed that management of symptoms can likewise be achieved. By management of symptoms, it is intended that the severity of symptoms can be maintained (i.e., worsening or advancement of symptoms is controlled) or, more preferably, the severity of symptoms can be reduced either in whole or in part.

The symptoms include: headache, seizures, hemorrhages and focal neurological symptoms.

Any of one or more different inhibitors of polycomb can be used, as well as combinations thereof. These can include, without limitation, small molecule inhibitors, protein and peptide inhibitors, and antisense (RNAi) inhibitors.

The pharmaceutical compositions of the present invention are preferably in the form of a single unit dosage form that contains an amount of the therapeutic agent that is effective to treat and/or prevent an endothelial to mesenchymal transition associated pathology of the type described herein. The pharmaceutical composition can also include suitable excipients, or stabilizers, and can be in solid or liquid form such as, tablets, capsules, powders, solutions, suspensions, or emulsions. Typically, the composition will contain from about 0.01 to 99 percent, preferably from about 5 to 95 percent of active compound(s), together with the carrier. The therapeutic agent, when combined with a suitable carrier and any excipients or stabilizers, and whether administered alone or in the form of a composition, can be administered orally, parenterally, subcutaneously, transdermally, intravenously, intramuscularly, intraperitoneally, by intranasal instillation, by implantation, by intracavitary or intravesical instillation, intraocularly, intraarterially, intralesionally, by application to mucous membranes, such as, that of the nose, throat, and bronchial tubes (i.e., inhalation), or by intracerebral administration.

For most therapeutic purposes, the therapeutic can be administered orally as a solid or as a solution or suspension in liquid form, via injection as a solution or suspension in liquid form, or via inhalation of a nebulized solution or suspension.

The solid unit dosage forms containing the therapeutic agent can be of a conventional type. The solid form can be a capsule, such as an ordinary gelatin type containing the therapeutic agent and a carrier, for example, lubricants and inert fillers such as, lactose, sucrose, or cornstarch. In another embodiment, the therapeutic agent is tableted with conventional tablet bases such as lactose, sucrose, or cornstarch in combination with binders like acacia or gelatin, disintegrating agents such as cornstarch, potato starch, or alginic acid, and a lubricant such as stearic acid or magnesium stearate.

For injectable dosages, solutions or suspensions of the therapeutic agent can be prepared in a physiologically and pharmaceutically acceptable diluent as the carrier. Such carriers include sterile liquids, such as water and oils, with or without the addition of a surfactant and other pharmaceutically and physiologically acceptable components, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solutions, and glycols, such as propylene glycol or polyethylene glycol, are preferred liquid carriers, particularly for injectable solutions.

For use as aerosols, the therapeutic agent in solution or suspension may be packaged in a pressurized aerosol container together with suitable propellants, for example, hydrocarbon propellants like propane, butane, or isobutane with conventional adjuvants. The therapeutic agent also may be administered in a non-pressurized form such as in a nebulizer or atomizer.

In addition to the above-described formulations which are intended to immediately deliver the therapeutic agents to the patient, sustained release formulations are also contemplated. Preferably, the sustained release formulation is an implantable device that includes a matrix in which the therapeutic agent is captured. Release of the agents can be controlled via selection of materials and the amount of drug loaded into the vehicle. A number of suitable implantable delivery systems are known in the art, such as U.S. Pat. No. 6,464,687 to Ishikawa et al., U.S. Pat. No. 6,074,673 to Guillen, each of which is hereby incorporated by reference in its entirety.

Implantable, sustained release drug delivery systems can be formulated using any suitable biocompatible matrix into which an agent can be loaded for sustained-release delivery. These include, without limitation, microspheres, hydrogels, polymeric reservoirs, cholesterol matrixes, polymeric systems and non-polymeric systems, etc. Exemplary polymeric matrixes include, without limitation, poly(ethylene-co-vinyl acetate), poly-L-lactide, poly-D-lactide, polyglycolide, poly(lactide-co-glycolide), polyanhydride, polyorthoester, polycaprolactone, polyphospagene, proteinaceous polymer, polyether, silicone, and combinations thereof.

Alternatively, for DNA-based therapeutic agents, one suitable vehicle for delivering the therapeutic agent includes solubilized cholesterol as an additive for DNA complexed with a cationic lipid, a cationic polymer, or a dendrimer. Preferably, the cholesterol is solubilized using a cyclodextrin, preferably methyl-[beta]-cyclodextrin. This type of formulation is described in U.S. Patent Publ No. 20020146830 to Esuvaranathan et al., which is hereby incorporated by reference in its entirety.

Thus, the present invention also relates to formulations and therapeutic systems comprising two or more active agents, one of which is the inhibitor of polycomb. Preferred inhibitors of the invention are selected from: PTC-209, UNC1999, GSK126, PRT 4165, PTC-596, DZNep, Ell, EPZ005687, GSK343, EPZ-6438, Stabilized α-helix of EZH2 peptide (SAH-EZH2), CPI-169, JQEZ-5, KM-301 and ORS-1.

Analogs or derivatives are compounds similar in structure but different in respect to elemental composition.

The present invention also comprised pharmaceutically acceptable salts of preferred compounds.

"Pharmaceutically acceptable salts" comprise conventional non-toxic salts obtained by salification with organic or inorganic bases. The inorganic salts are, for example, metal salts, particularly alkali metal salts, alkaline-earth metal salts and transition metal salts (such as sodium, potassium, calcium, magnesium, aluminum). Salts may be also obtained with bases, such as ammonia or secondary or tertiary amines (such as diethylamine, triethylamine, piperidine, piperazine, morpholine), or with basic amino-acids, or with osamines (such as meglumine), or with aminoalcohols (such as 3-aminobutanol and 2-aminoethanol).

In addition, the compounds of the present invention can exist in unsolvated as well as in solvated forms with pharmaceutically acceptable solvents such as water, ethanol and the like.

The invention also comprises pharmaceutical compositions characterized by containing one or more active principles selected from sulindac, sulindac sulfide, sulindac sulfone, phospho-sulindac, phospho-sulindac sulphide, phospho-sulindac sulfone, silibinin, curcumin, resveratrol, salinomycin, and propranolol in association with pharmaceutically acceptable carrier, excipients and diluents for the use in the treatment of an endothelial to mesenchymal transition associated pathology.

Administration through synthetic nanoparticles engineered to target pathological endothelial cells, for example expressing EndMT markers as in CCM lesions (such as Klf4, Klf2, Ly6a, S100a4, CD44, Id1, a-SMA, Snai1, Snai2 PAI1, N-cadherin, Zeb2, other markers are indicated in Fadini et al, 2012: Margariti et al, 2012; Li et al, 2012; Liang et al 2011; Stein et al, 2006; Medici et al, 2012) is also comprised within the present invention (Davis et al, 2010, Nature 464, 1067-1071; Dashi et al, 2012 Adv Mater., 24, 3864-3869). Small molecules, proteins, peptide, antisense nucleic acid may be encapsulated in such nanoparticles.

The above mentioned uses and methods also include the possibility of co-administration of additional therapeutic agents, simultaneously or delayed with respect to the administration of the compounds.

In the previously mentioned uses and methods, the dosage of the inhibitor can vary depending upon a variety of factors including the patient type and condition, the degree of disease severity, mode and time of administration, diet and drug combinations. As an indication, they can be administered within a dose range of between 0.001 and 1000 mg/kg/day. The determination of optimum dosages for a particular patient is well known to one skilled in the art. Preferred dose range is between 1 and 10 mg/kg/day, most preferred range is between 10 and 100 mg/kg/day. Still preferred dose range is between 100 and 200 mg/kg/day. Yet preferred dose range is between 200 and 500 mg/kg/day. Still preferred dose range is between 500 and 1000 mg/kg/day. Preferably the inhibitor of the invention is administered orally.

As is common practice, the compositions are normally accompanied by written or printed instructions for use in the treatment in question.

BRIEF DESCRIPTION OF THE DRAWINGS

The present invention will be illustrated by means of non-limiting examples and figures.

(A) Representative image of western blot analysis of Bmi1 on lysates from confluent wild type (WT) and CCM3 knockout (CCM3-KO) cells. Vinculin was used as loading control. (B) Relative quantification of western blot analysis. Data are expressed as average±standard error (SE) of three independent experiments. * p<0.05.

Figure 2:
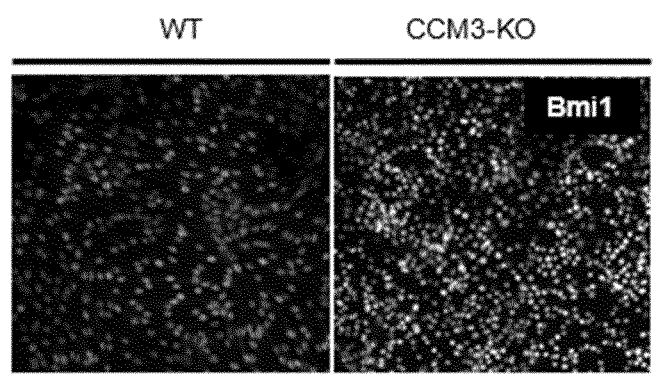

FIG. 2. Bmi1 was upregulated in CCM3 knockout cells compare to wild type cells.

Representative immunostaining for nuclear Bmi1 in wild type and CCM3 knockout cells. Image was acquired at 20× magnification with confocal microscope.

Figure 3:
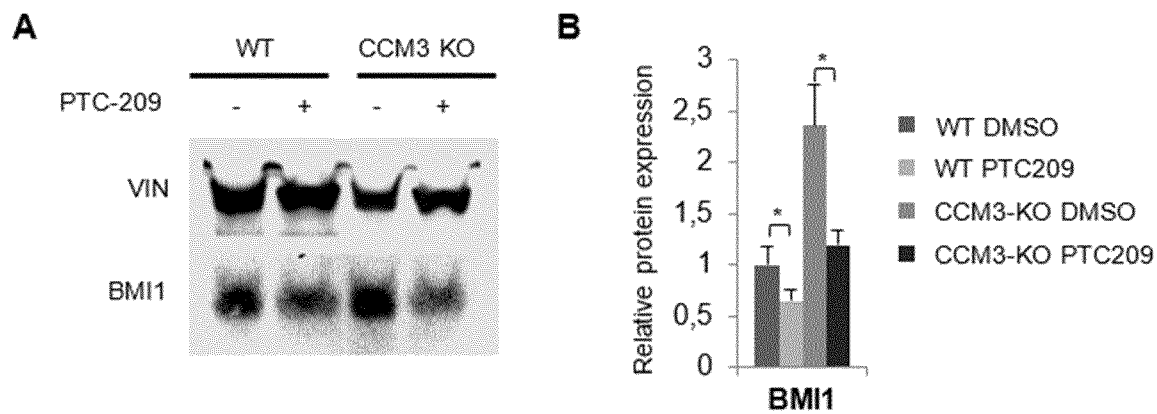

FIG. 3. Bmi1 was upregulated in CCM3 knockout cells compare to wild type cells.

(A) Representative image of western blot analysis of Bmi1 on lysates from confluent wild type (WT) and CCM3 knockout (CCM3-KO) cells treated with PTC209 for 24 hours. Vinculin (housekeeper) was used as loading control. (B) Relative quantification of western blot analysis. Data are expressed as average±SE of three independent experiments. * p<0.05.

Figure 4:
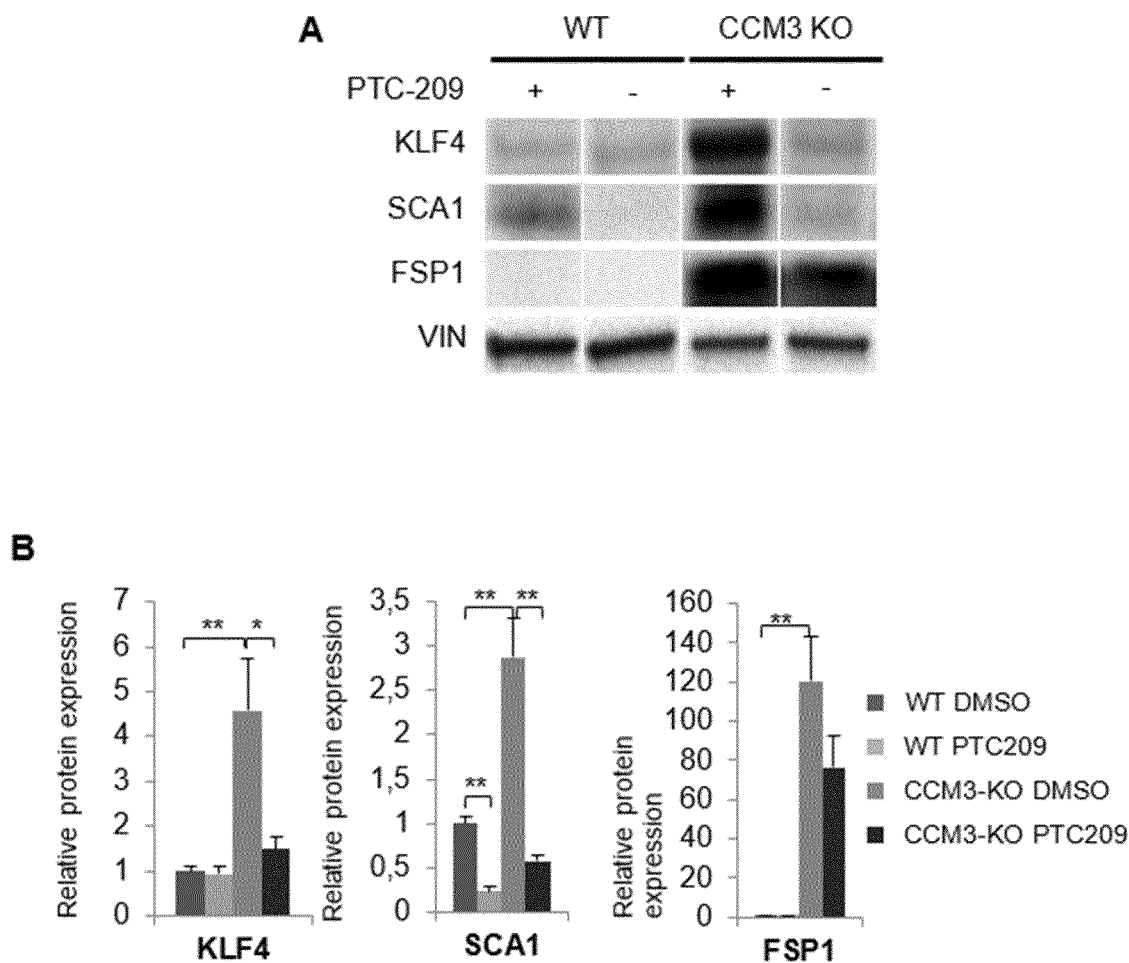

FIG. 4. Bmi1 inhibition reduced EndMT markers in CCM3 knockout cells.

(A) Representative image of western blot analysis of EndMT markers (Klf4, Sca1 and Fsp1) on lysates from confluent wild type (WT) and CCM3 knockout (CCM3-KO) cells treated with PTC209 for 72 hours. Vinculin (housekeeper) was used as loading control. (B) Relative quantification of western blot analysis. Data are expressed as average±SE of three independent experiments. * p<0.05; ** p<0.01.

Figure 5:
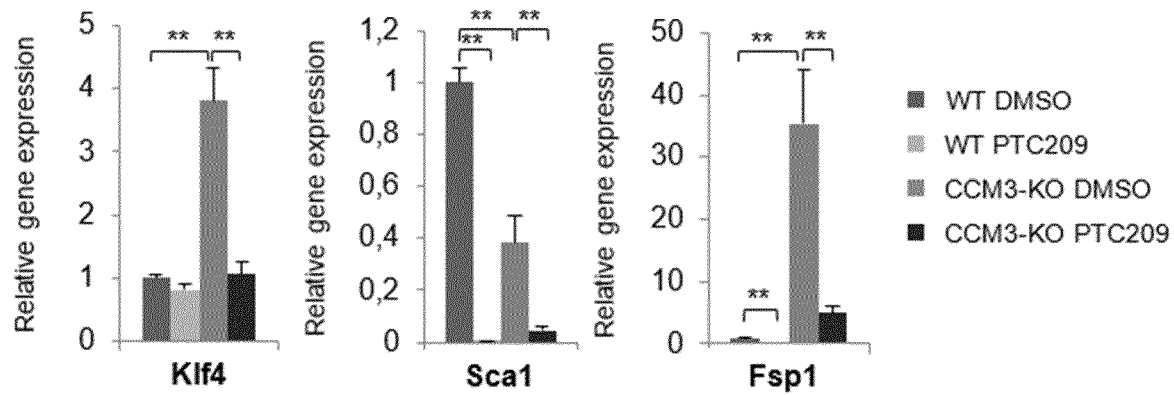

FIG. 5. Bmi1 inhibition reduced EndMT markers in CCM3 knockout cells.

Transcript of Klf4, Sca1 and Fsp1 were analysed by RT-PCR after PTC209 treatment for 72 hours. Data are expressed as the average±SE of the fold enrichment of three independent experiments. *P<0.05; **P<0.01.

Figure 6:
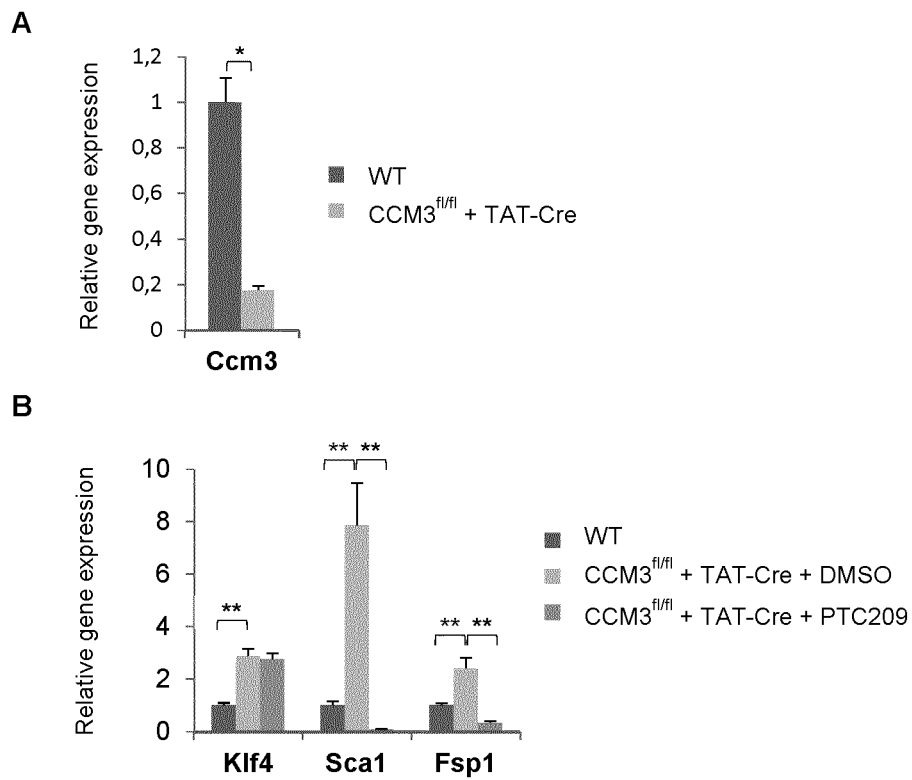

FIG. 6. Bmi1 inhibition reduced EndMT markers expression in freshly isolated brain endothelial cells knockout for CCM3.

(A) Transcript of Ccm3 was analysed by RT-PCR. Ccm3 decreased in CCM3fl/fl brain endothelial cells treated with TAT-Cre recombinase but not in wild type. (B) Klf4, Sca1 and Fsp1 transcripts were analysed by RT-PCR after PTC209 treatment for 72 hours. Data are expressed as the average±SE of the fold enrichment of three independent experiments. *p<0.05; ** p<0.01.

Figure 7:
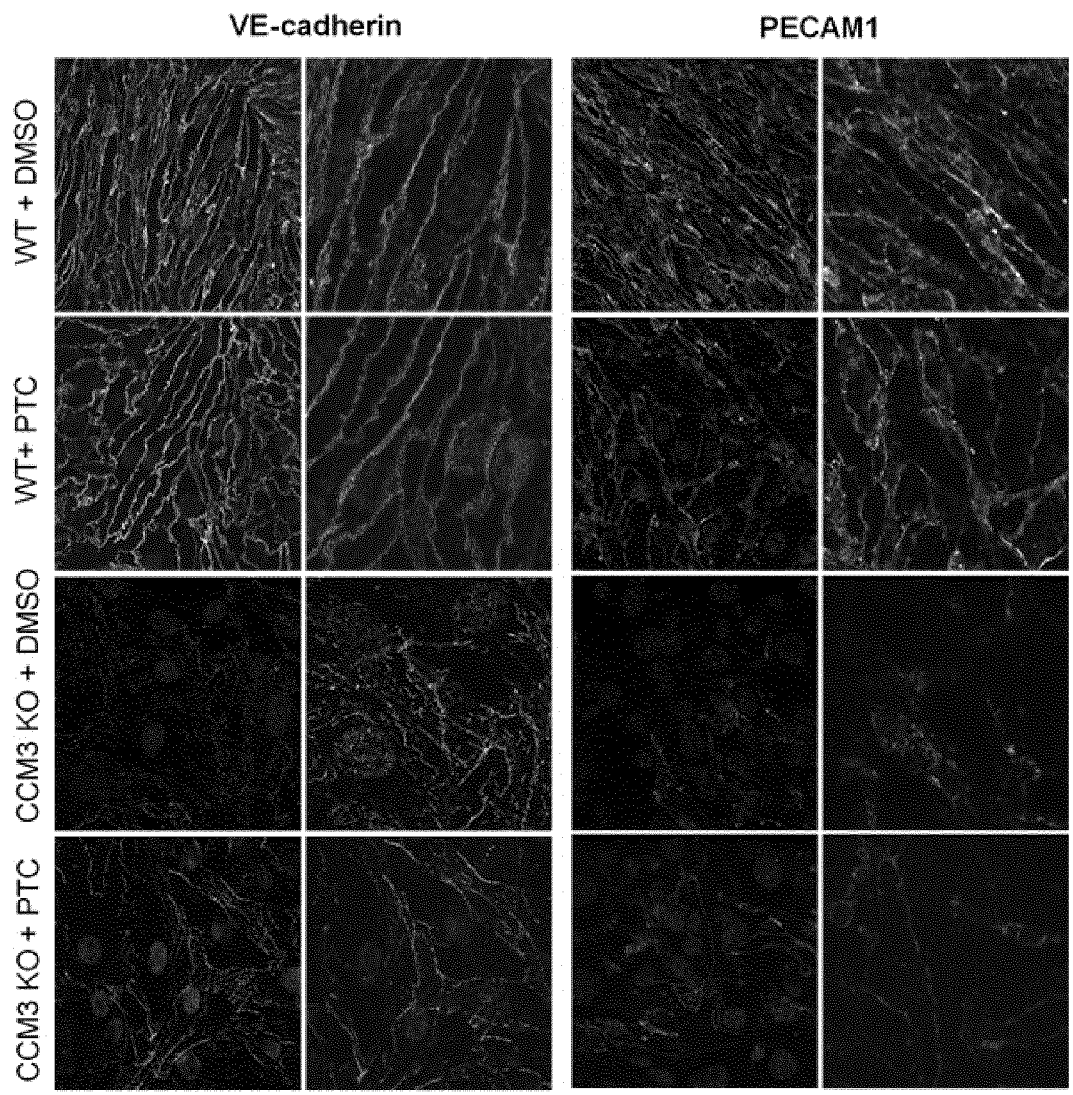

FIG. 7. Bmi1 inhibition did not rescue disorganisation of junctions in CCM3 knockout cells.

Representative immunostaining for VE-cadherin and PECAM1 on immortalized lung wild type (WT) and CCM3 knockout (CCM3 KO) endothelial cells, treated with PTC209 or DMSO. Image was acquired at 40× (panels on the left) and 60× (panels on the right) magnification with confocal microscopy.

Figure 8:
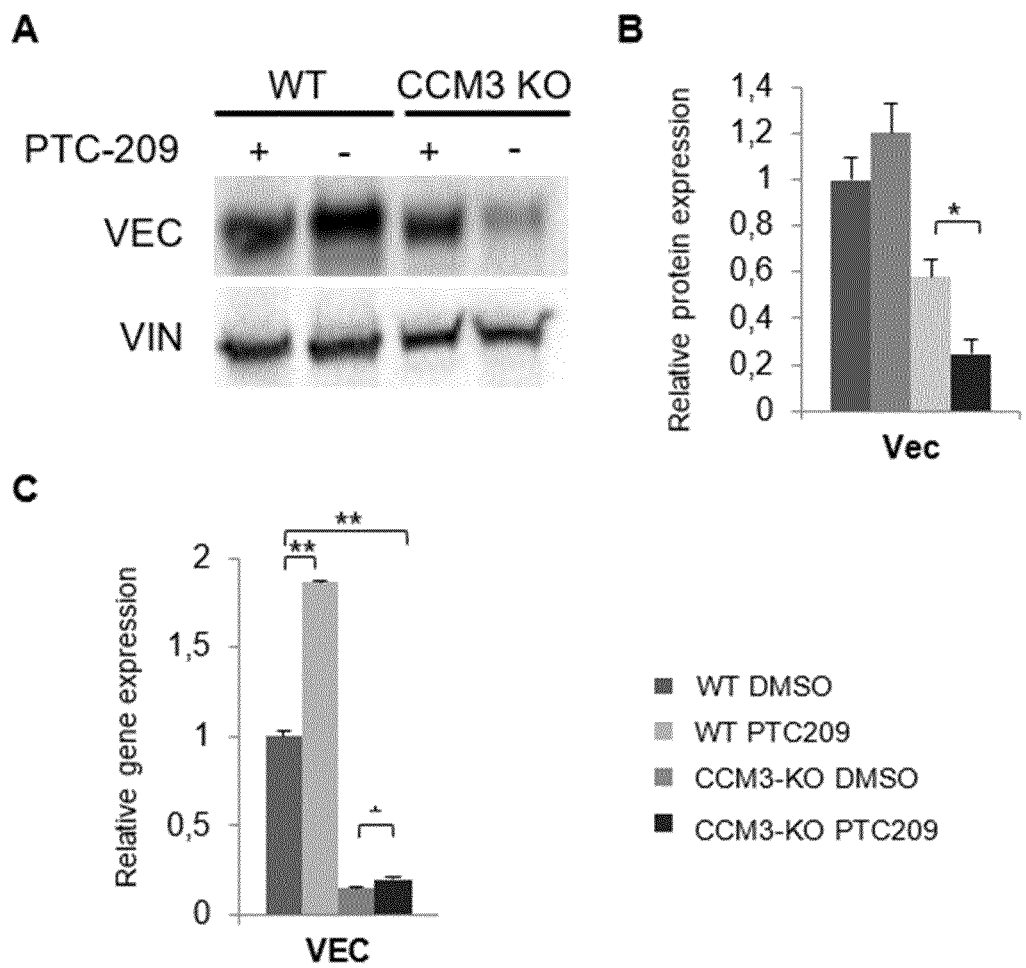

FIG. 8. Bmi1 inhibition was not enough to rescue VE-cadherin and PECAM1 downregulation in CCM3 KO cells.

(A) Representative image of western blot analysis of VE-cadherin on lysates from confluent wild type (WT) and CCM3 knockout (CCM3-KO) cells treated with PTC209 for 72 hours. Vinculin was used as loading control. (B) Relative quantification of western blot analysis. Data are expressed as average±ED of three independent experiments.

(C) VE-cadherin transcript were analysed by RT-PCR after PTC209 treatment. Data are expressed as the average±ED of the fold enrichment of three independent experiments. *p<0.05; ** p<0.01.

Figure 9:
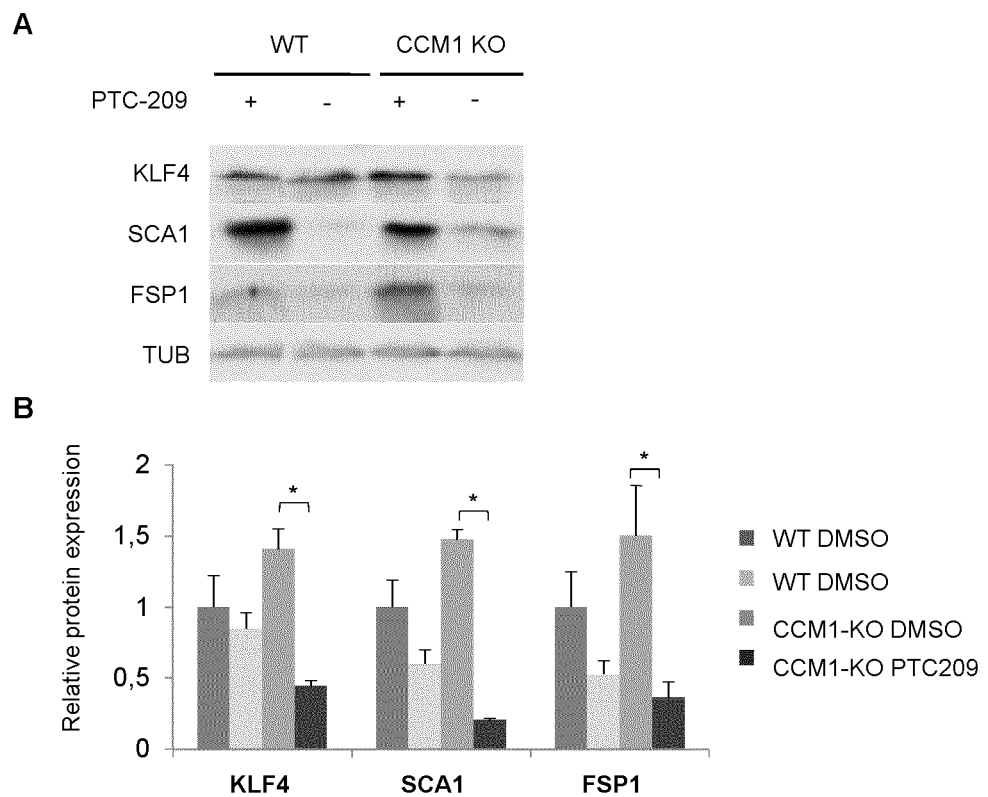

FIG. 9. Bmi1 inhibition reduced EndMT markers in CCM1 knockout cells.

(A) Representative image of western blot analysis of EndMT markers (Klf4, Sca1 and Fsp1) on lysates from confluent wild type (WT) and CCM1 knockout cells (CCM1-KO) treated with PTC209 for 72 hours. Tubulin was used as loading control. (B) Relative quantification of western blot analysis. Data are expressed as average±ED of three independent experiments. * p<0.05.

Figure 10:
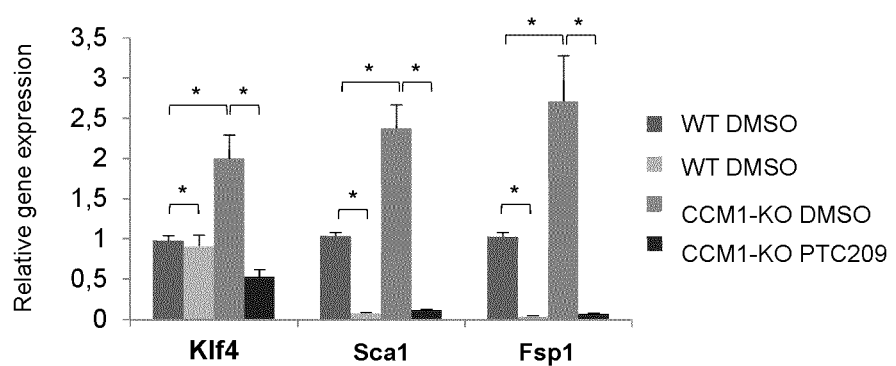

FIG. 10. Bmi1 inhibition reduced EndMT markers in CCM1 knockout cells.

Transcript of Klf4, Sca1 and Fsp1 were analysed by RT-PCR after PTC209 treatment for 72 hours. Data are expressed as the average±ED of the fold enrichment of three independent experiments. * p<0.05.

Figure 11:
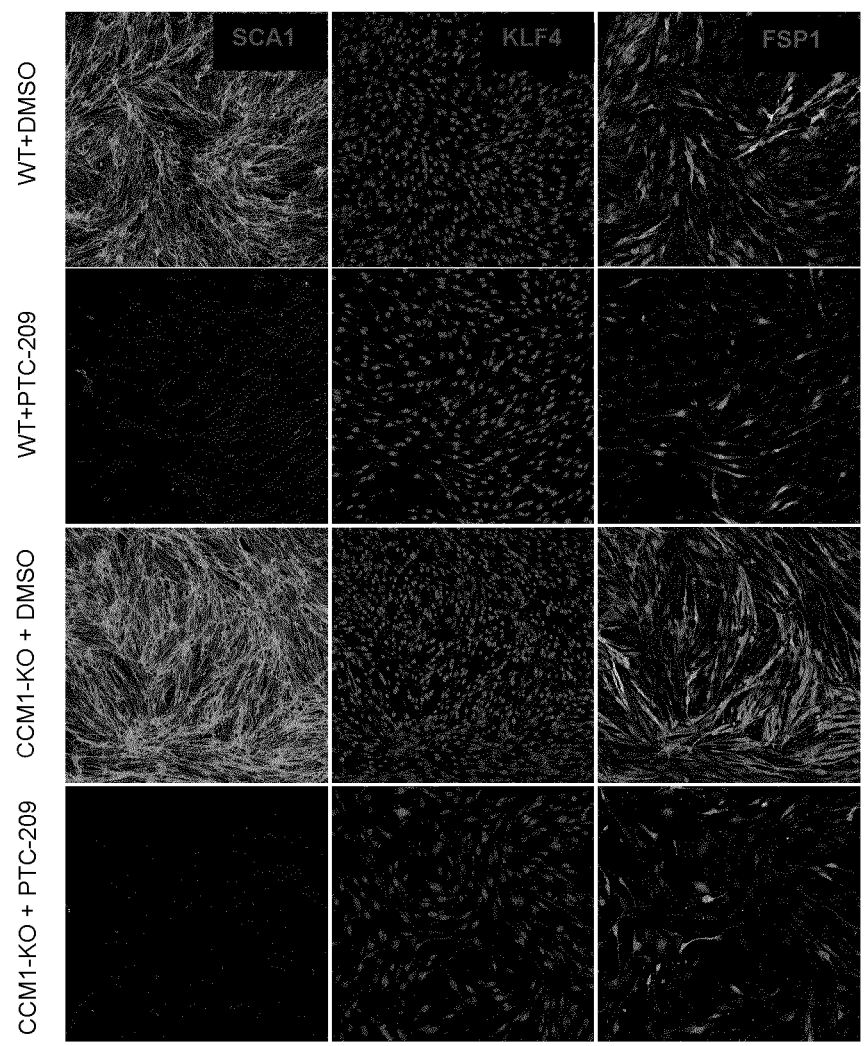
Figure 11:
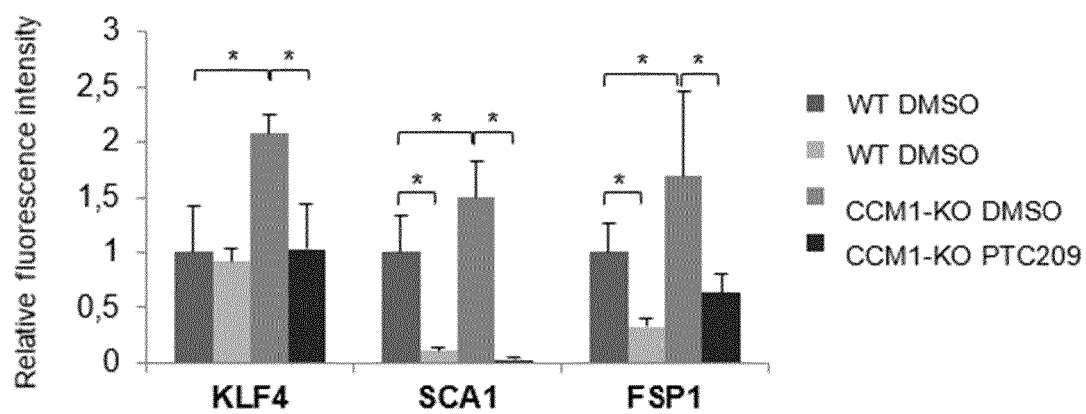

FIG. 11. Bmi1 inhibition reduced EndMT markers in CCM1 knock out cells-immunofluorescence analysis.

Representative immunostaining of Sca1 (green), Klf4 (red) and Fsp1 (pink) on wild type (WT) and immortalized lung endothelial cells CCM1 knockout (CCM1 KO), treated with PTC209 or DMSO. Image was acquired at 20× magnification with confocal microscopy. (B) Relative quantification of the relative fluorescence intensity of staining of panel A. Data are expressed as the average±ED of the relative fluorescence intensity of three fields per glass slide. Data were normalized on the fluorescence of WT cells. * p<0.05, ** p<0.01.

Figure 12:
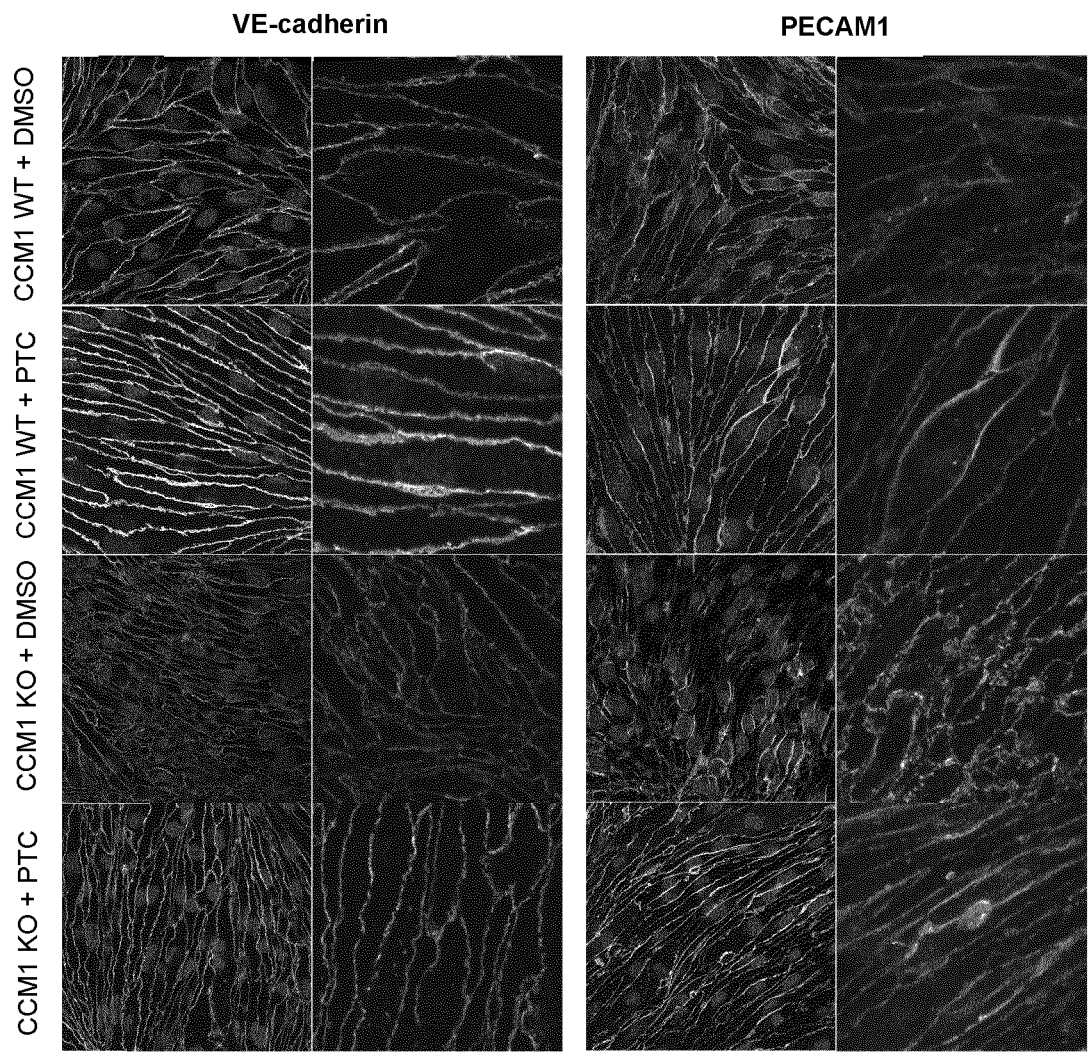

FIG. 12. Bmi1 inhibition partially rescued disorganisation of junctions in CCM1 knockout cells.

Representative immunostaining of DAPI (blue), VE-cadherin (grey) and PECAM1 (grey) on wild type (WT) and immortalized lung endothelial cells CCM1 knockout (CCM1 KO), treated with PTC209 or DMSO. Image was acquired at 60× magnification with confocal microscopy.

Figure 13:
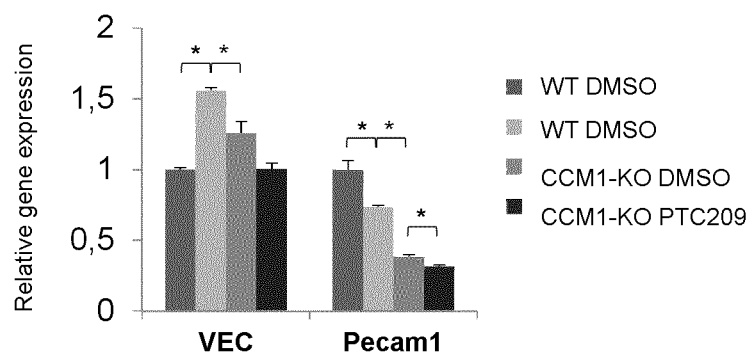

FIG. 13. Bmi1 inhibition did not affect VE-cadherin and PECAM1 gene expression in CCM1 KO cells.

VE-cadherin and Pecam1 transcripts were analysed by RT-PCR after PTC209 treatment. Data are expressed as the average±ED of the fold enrichment of three independent experiments. * p<0.05.

Figure 14:
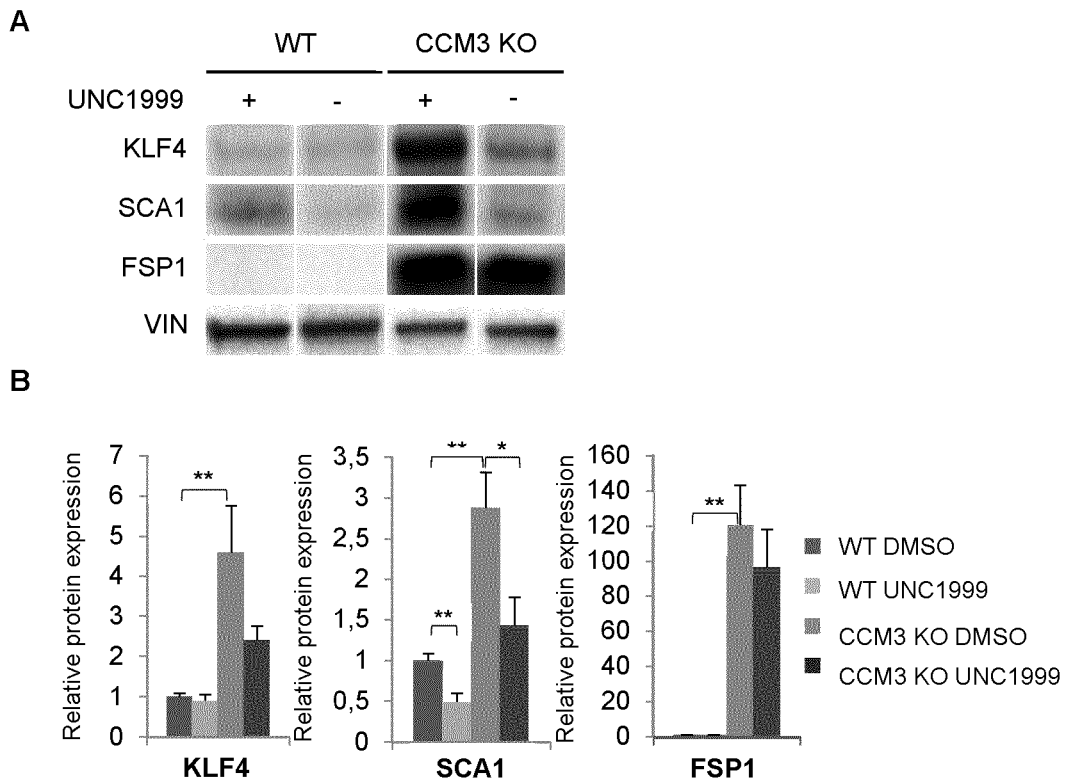

FIG. 14. Ezh1/2 inhibition reduced EndMT markers in CCM3 knockout cells.

Representative image of western blot analysis of EndMT markers (Klf4, Sca1 and Fsp1) on lysates from confluent wild type (WT) and CCM3 knockout (CCM3-KO) cells treated with UNC1999 for 72 hours. Vinculin (housekeeper) was used as loading control. (B) Relative quantification of western blot analysis. Data are expressed as average±ED of three independent experiments. * p<0.05; ** p<0.01.

Figure 15:
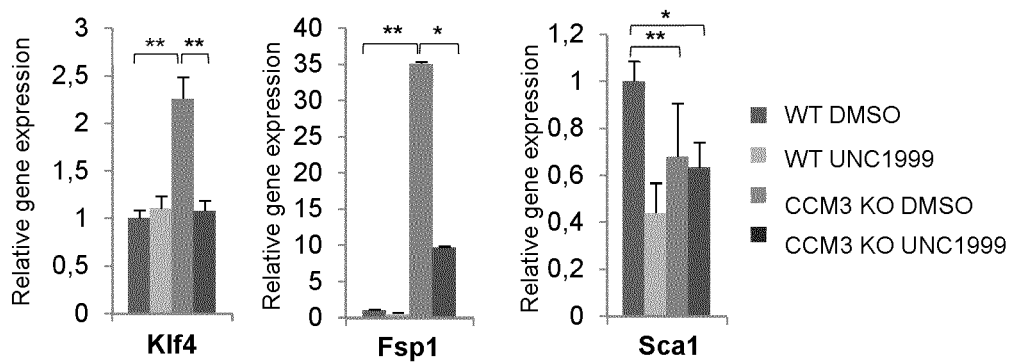

FIG. 15. Ezh1/2 inhibition reduced EndMT markers in CCM3 knockout cells.

Transcript of Klf4, Sca1 and Fsp1 were analysed by RT-PCR after PTC209 treatment for 72 hours. Data are expressed as the average±ED of the fold enrichment of three independent experiments. * p<0.05; ** p<0.01.

Figure 16:
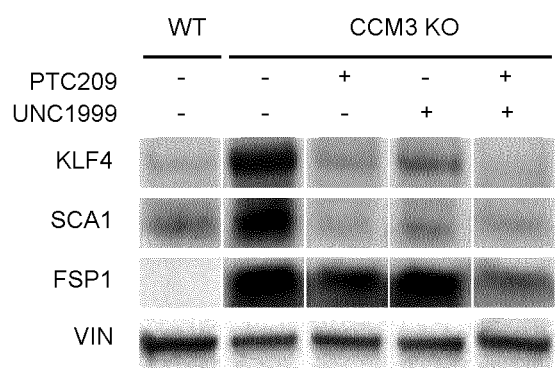
Figure 16:
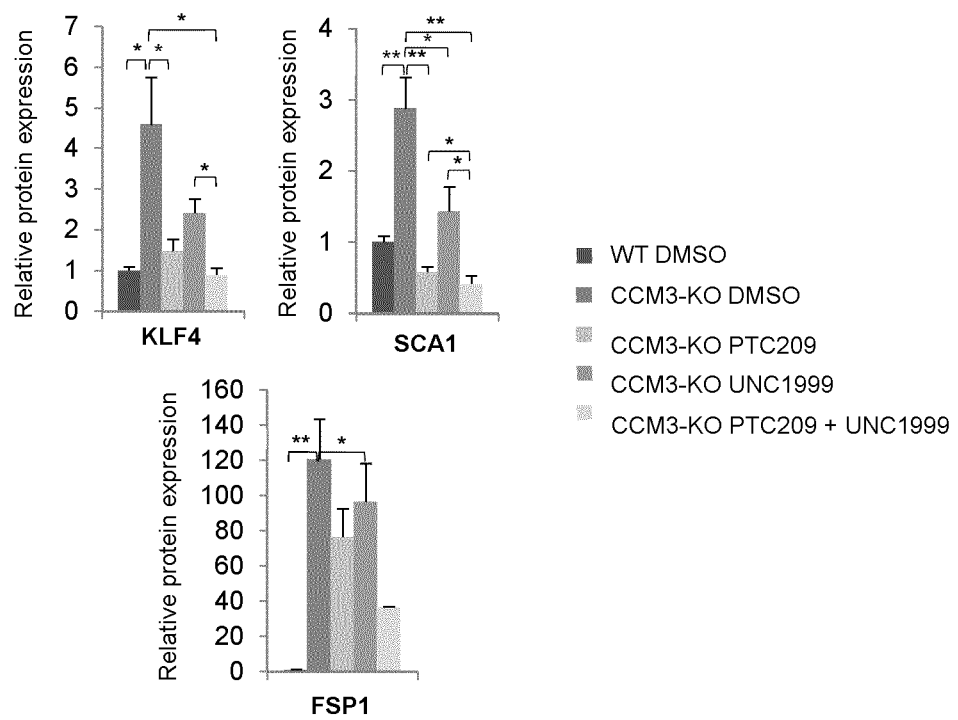

FIG. 16. Combine Bmi1 and Ezh1/2 inhibition reduced EndMT markers in CCM3 knockout cells.

(A) Representative image of western blot analysis of EndMT markers (Klf4, Sca1 and Fsp1) on lysates from confluent wild type (WT) and CCM3 knockout (CCM3-KO) cells treated with PTC209, UNC1999 or the combination of both for 72 hours. Vinculin was used as loading control. (B) Relative quantification of western blot analysis. Data are expressed as average ±ED of three independent experiments. * p<0.05; ** p<0.01.

Figure 17:
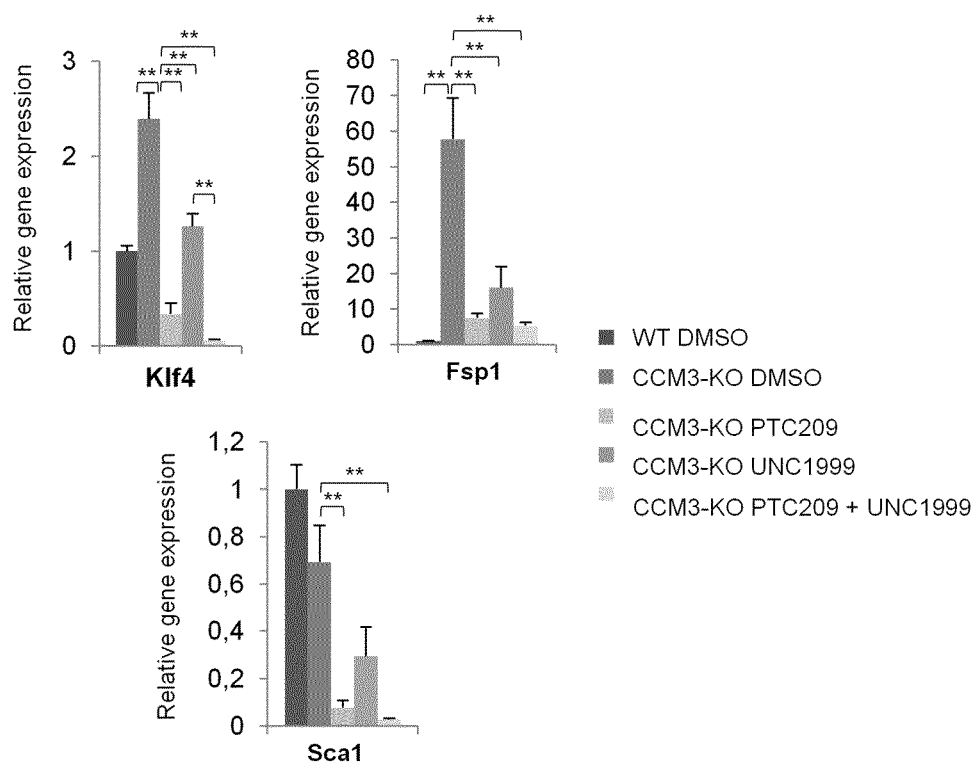

FIG. 17. Combine Bmi1 and Ezh1/2 inhibition reduced EndMT markers in CCM3 knockout cells.

Transcript of Klf4, Sca1 and Fsp1 were analysed by RT-PCR after PTC209, UNC1999 or the combination of PTC209 and UNC1999 treatment for 72 hours. Data are expressed as the average±ED of the fold enrichment of three independent experiments. * p<0.05; ** p<0.01.

Figure 18:
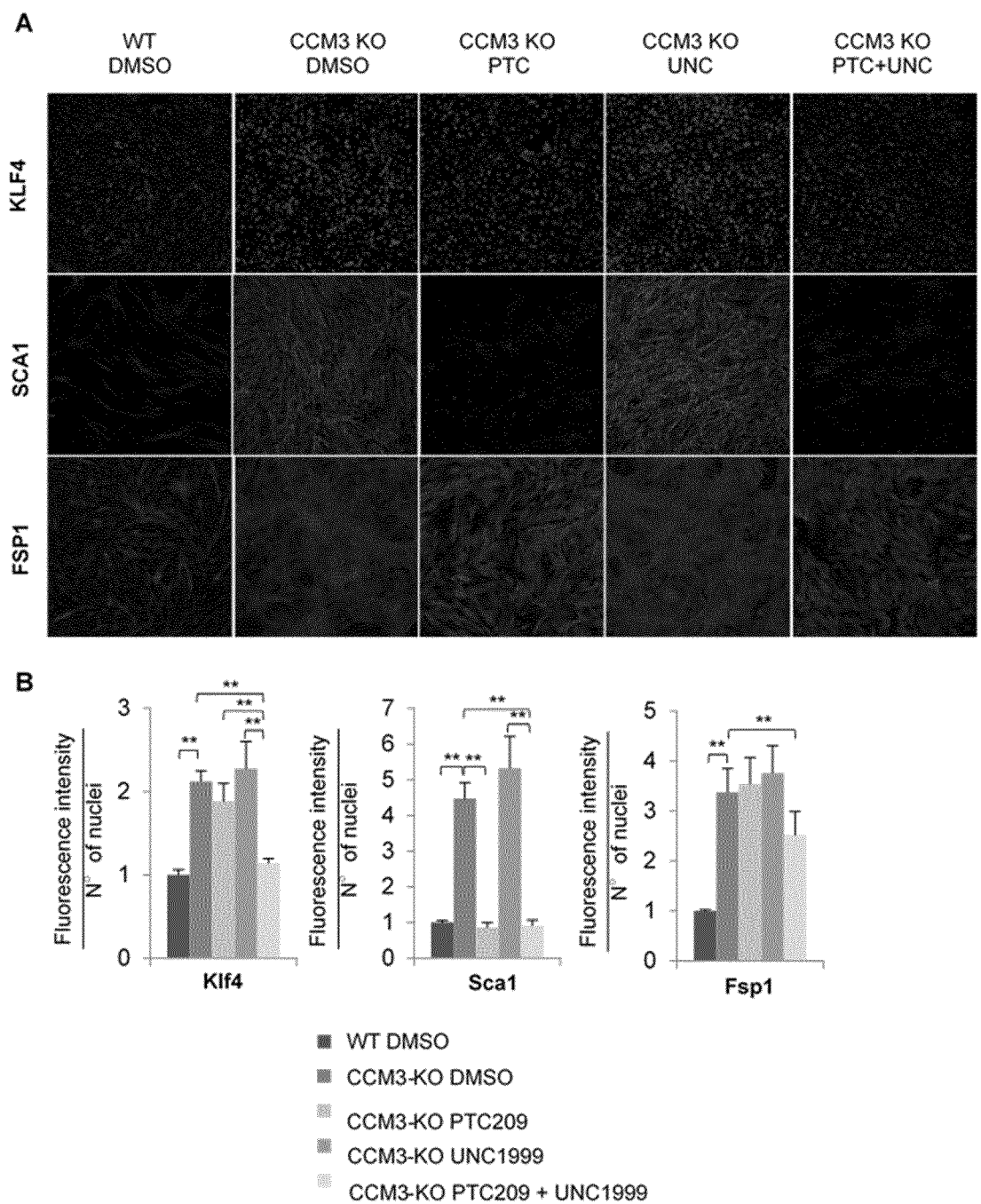

FIG. 18. Combine Bmi1 and Ezh1/2 reduced EndMT markers in CCM3 knock out cells.

(A) Representative immunostaining of Sca1, Klf4 and Fsp1 antibody (red) on wild type (WT) and immortalized lung endothelial cells CCM3 knockout (CCM1 KO), treated with PTC209, UNC1999 or the combination of the two drugs. Image was acquired at 20× magnification with confocal microscopy. (B) Relative quantification of the relative fluorescence intensity. Data are expressed as the average±ED of the relative fluorescence intensity of three fields per glass slide. Data were normalized on the fluorescence of WT cells. *P<0.05, **P<0.01.

Figure 19:
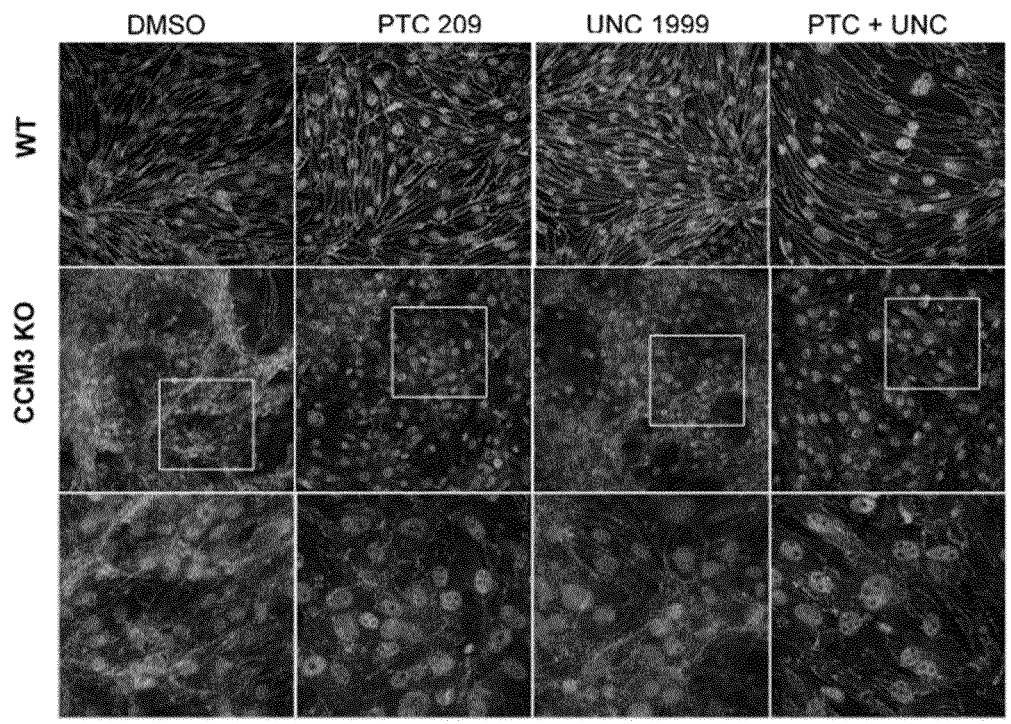

FIG. 19. Combine Bmi1 and Ezh1/2 partially rescued junctional disorganisation in CCM3 knock out cells.

(A) Representative immunostaining of DAPI (blue) and VE-cadherin (green) on wild type (WT) and immortalized lung endothelial cells CCM3 knockout (CCM3 KO), treated with PTC209, UNC1999 or the combination of the two drugs. Image was acquired at 20× magnification with confocal microscopy. Areas marked by a square were enlarged (60×) and show below each respective 20× magnification as insets.

Figure 20:
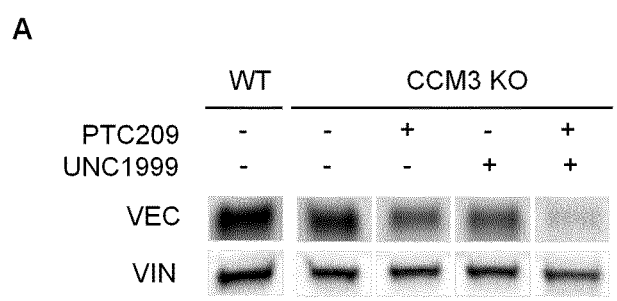
Figure 20:
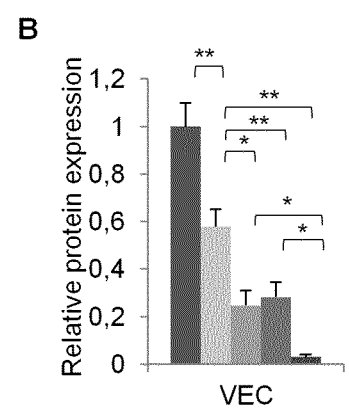

FIG. 20. Combine Bmi1 and Ezh1/2 inhibition did not rescue VE-cadherin protein expression level.

(A) Representative image of western blot analysis of VE-cadherin on lysates from confluent wild type (WT) and CCM3 knockout (CCM3-KO) cells treated with PTC209, UNC1999 or the combination of both for 72 hours. Vinculin was used as loading control. (B) Relative quantification of western blot analysis. Data are expressed as average±ED of three independent experiments. * p<0.05; ** p<0.01.

Figure 21:
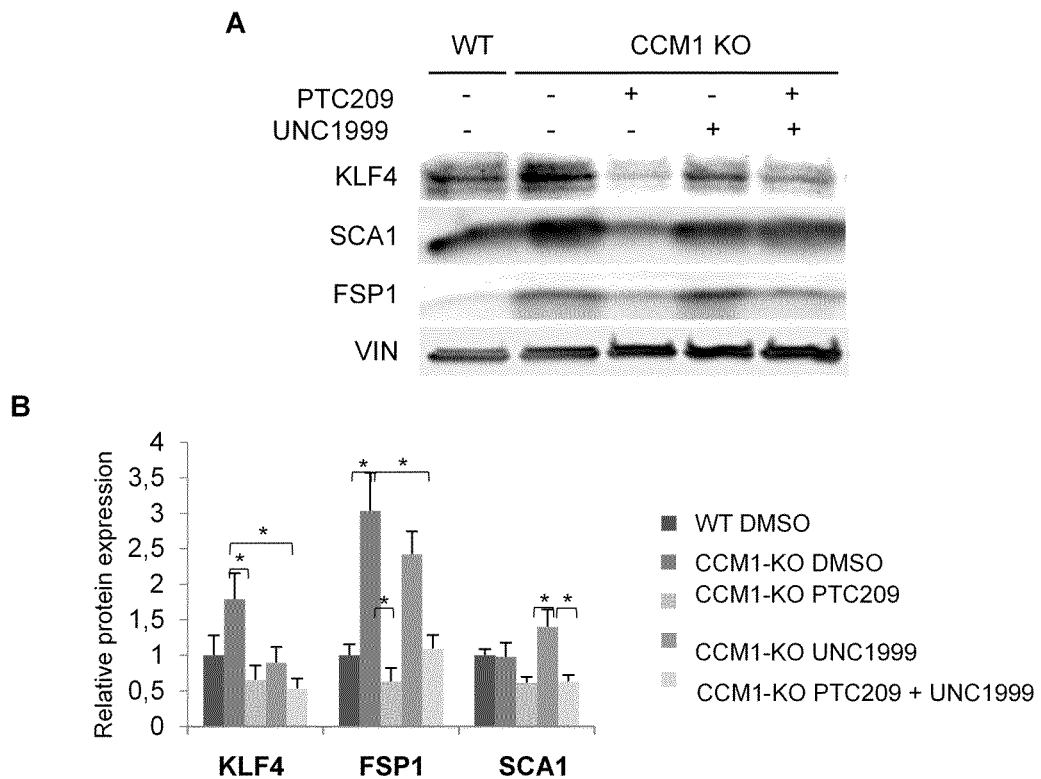

FIG. 21. Combine Bmi1 and Ezh1/2 inhibition reduced EndMT markers in CCM1 knockout cells.

(A) Representative image of western blot analysis of EndMT markers (Klf4, Sca1 and Fsp1) on lysates from confluent wild type (WT) and CCM1 knockout (CCM1-KO) cells treated with PTC209, UNC1999 or the combination of both for 72 hours. Vinculin was used as loading control. (B) Relative quantification of western blot analysis. Data are expressed as average ±ED of three independent experiments. * p<0.05.

Figure 22:
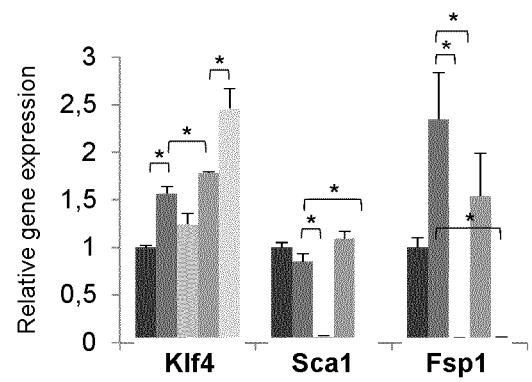

FIG. 22. Combine Bmi1 and Ezh1/2 inhibition reduced EndMT markers in CCM1 knockout cells.

Transcript of Klf4, Sca1 and Fsp1 were analysed by RT-PCR after PTC209, UNC1999 or the combination of PTC209 and UNC1999 treatment for 72 hours. Data are expressed as the average±ED of the fold enrichment of three independent experiments. * p<0.05.

Figure 23:
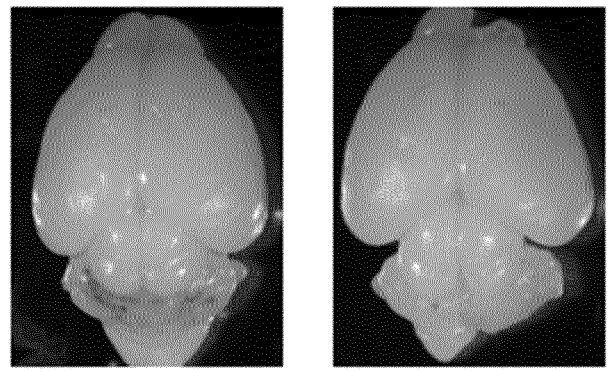
Figure 23:
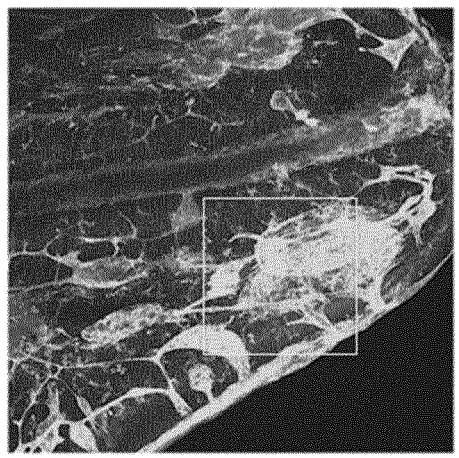
Figure 23:
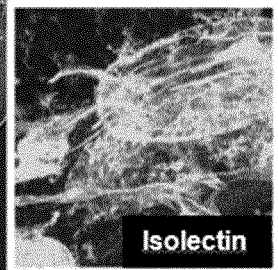
Figure 23:
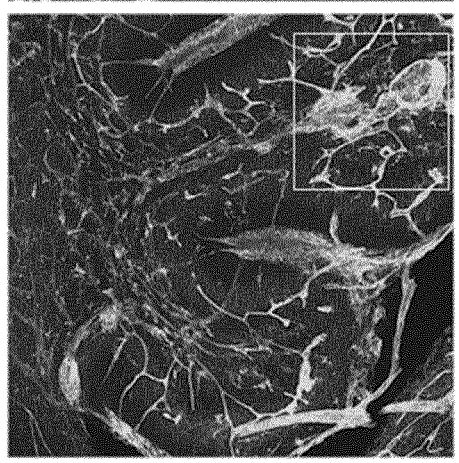
Figure 23:
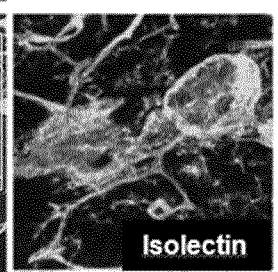

FIG. 23. Combine Bmi1 and Ezh1/2 reduced size and number of lesion in CCM3 knock out mice.

(A) Picture of the total brains taken under stereomicroscope of one CCM3 knock out mice treated with DMSO and one CCM3 knock out mice treated with PTC209 combined with UNC1999. (B) Representative immunostaining of Isolectin on brain section from CCM3 knockout mice treated with DMSO or the combination of PTC209 and UNC1999. Image was acquired at 40× magnification with confocal microscopy. Areas marked by a square were enlarged (60×) and show next to each respective 40× magnification as insets.

Figure 24:
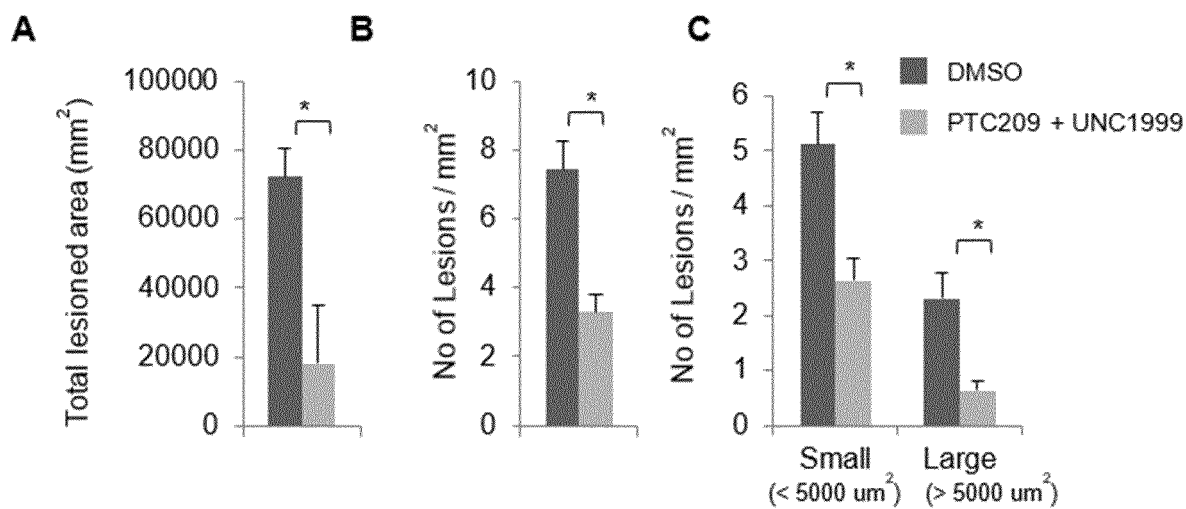

FIG. 24. Combine Bmi1 and Ezh1/2 reduced size and number of lesions and downregulated more large lesions, than small lesions, in CCM3 knock out mice.

(A) Assessment of average total lesioned area ($mm^2$) per brain, (B) number of lesions per $mm^2$ per brain and (C) Number of lesions per $mm^2$ dividing in small (<5000 $um^2$) and large (>5000 $um^2$) lesions per brain. * p<0.05; Number of lesion counted=1137, Number of animals=24

Figure 25:
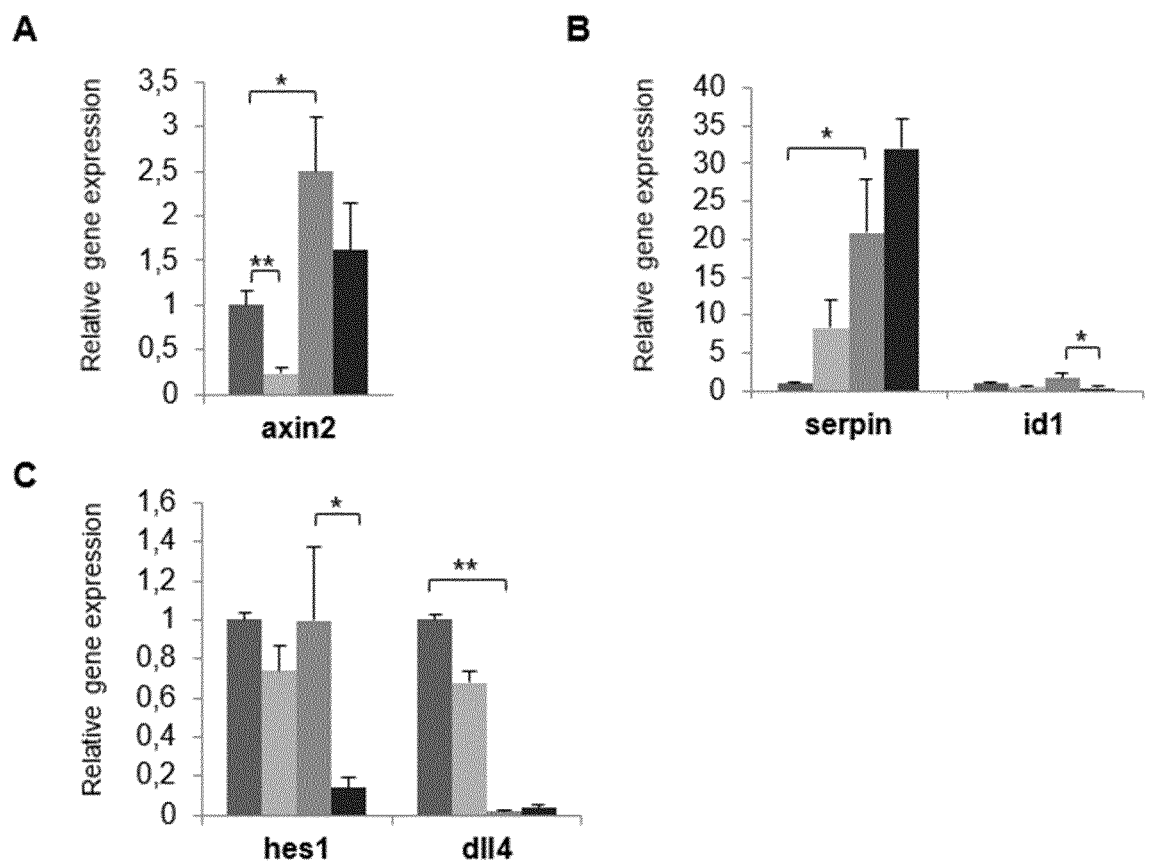

FIG. 25. Bmi1 inhibition reduced Axin2, Id1 and Hes1 activation in CCM3 knock out cells and did not Serpin1 expression.

Transcript of (A) Axin2, (B) Serpin1 and Id1 and (C) Hes1 and Dll4 were analysed by RT-PCR after PTC209 treatment for 72 hours. Data are expressed as the average±ED of the fold enrichment of three independent experiments. * p<0.05.

Figure 26:
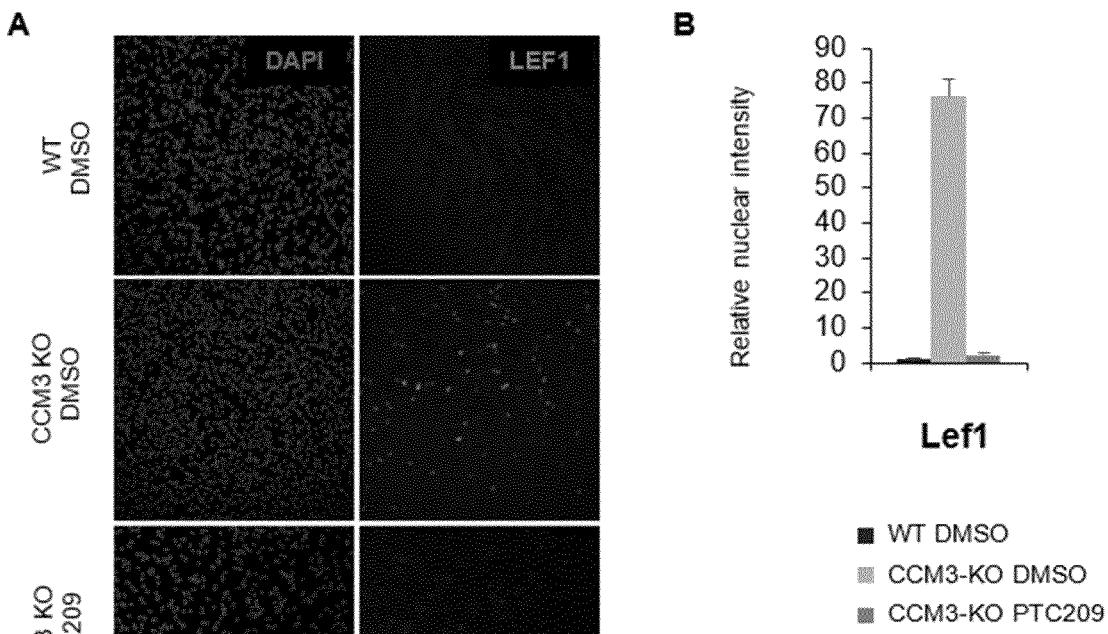

FIG. 26. Bmi1 inhibition reduced LEF1 in CCM3 knock out cells.

(A) Representative immunostaining of DAPI (blue) and LEF1 (green) on wild type (WT) and immortalized lung endothelial cells CCM3 knockout (CCM3 KO), treated with PTC209 or DMSO. Image was acquired at 20× magnification with confocal microscopy. (B) Relative quantification of the relative fluorescence intensity. Data are expressed as the average±ED of the relative fluorescence intensity of three fields per glass slide. Data were normalized on the fluorescence of WT cells.

Figure 27:
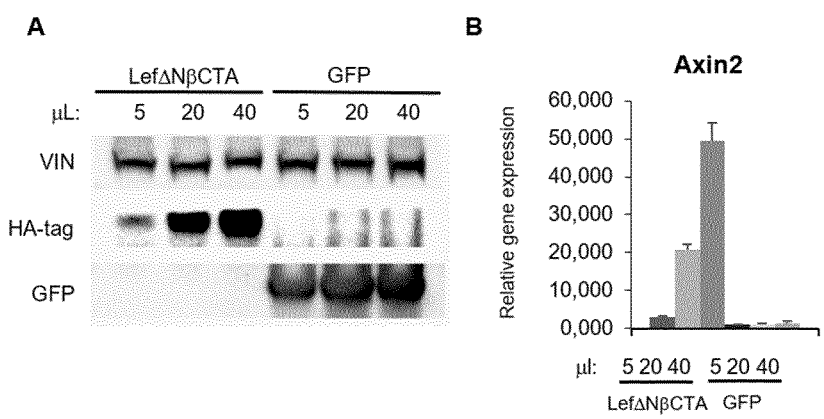

FIG. 27. Wild type cells responded to infection, with lentivirus expressing LefΔN-β-catΔC construct, upregulating Axin2 in a dose dependent manner.

(A) Representative image of western blot analysis of HA-tag and GFP on lysates from confluent wild type (WT) infected for six days with lentivirus expressing LefΔN-β-catΔC. Vinculin (housekeeper) was used as loading control. (B) Transcript of Axin2 was analysed by RT-PCR after six days of infection with lentivirus expressing LefΔN-β-catΔC. Data are expressed as the average±ED of the fold enrichment of three dependent experiments.

Figure 28:
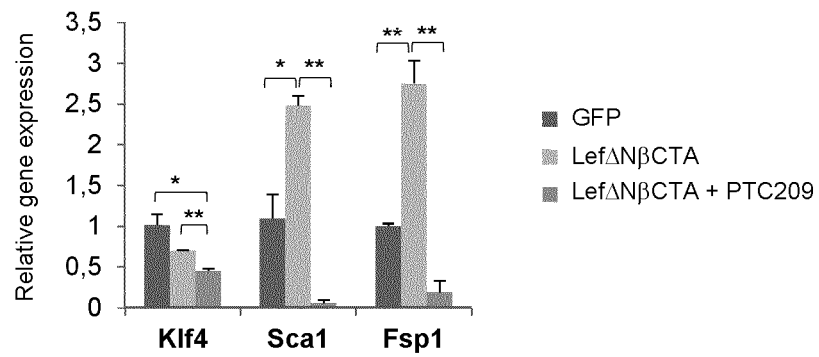

FIG. 28. Bmi1 inhibition reduced overexpression of EndMT markers resulting from infection with lentivirus expressing LefΔN-β-catΔC.

Transcript of Klf4, Sca1 and Fsp1, derived from wild type cells infected with lentivirus expressing LefΔN-β-catΔC and treated with PTC209 for 72 hours, were analysed by RT-PCR. Data are expressed as the average±ED of the fold enrichment of three independent experiments. * $p<0.05$; ** $p<0.01$.

Figure 29:
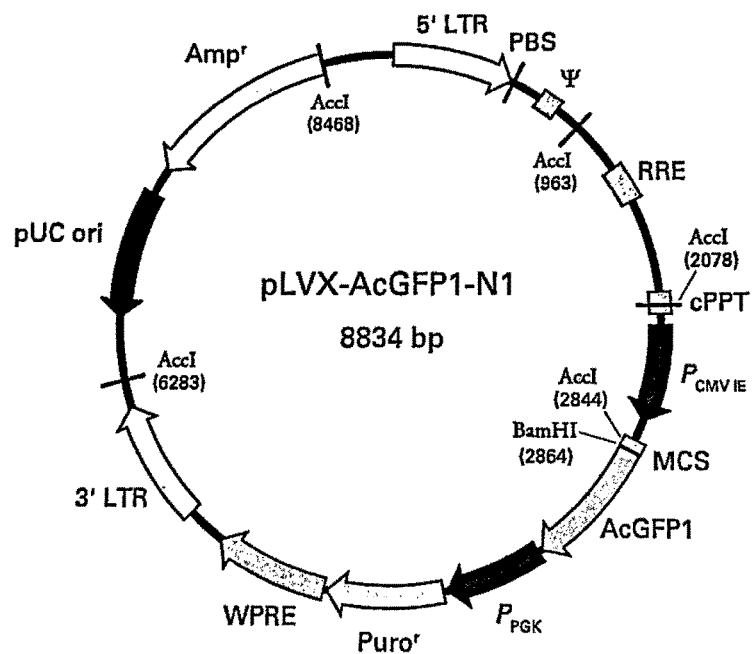

FIG. 29. pLVX-AcGFP1-N1. Schematic representation of the backbone of the pLVX-AcGFP1-N1 plasmid used for cloning.

Figure 30:
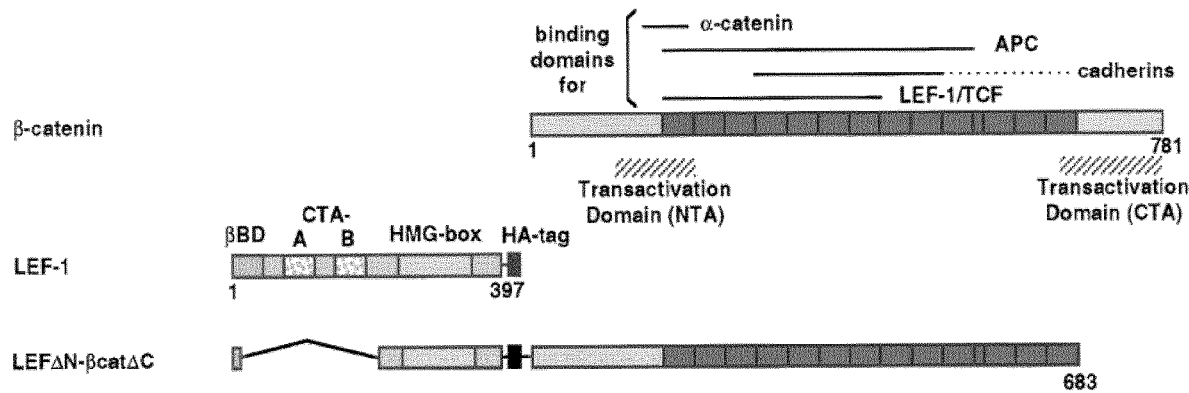

FIG. 30. LefΔN-β-catΔC. Schematic representation of the LefΔN-β-catΔC construct obtained by the fusion of the transcription factor LEF1 and the transactivation domain of the b-catenin. This is a constitutively active mutant that activate gene target transcription without playing any role at the membrane.

Figure 31:
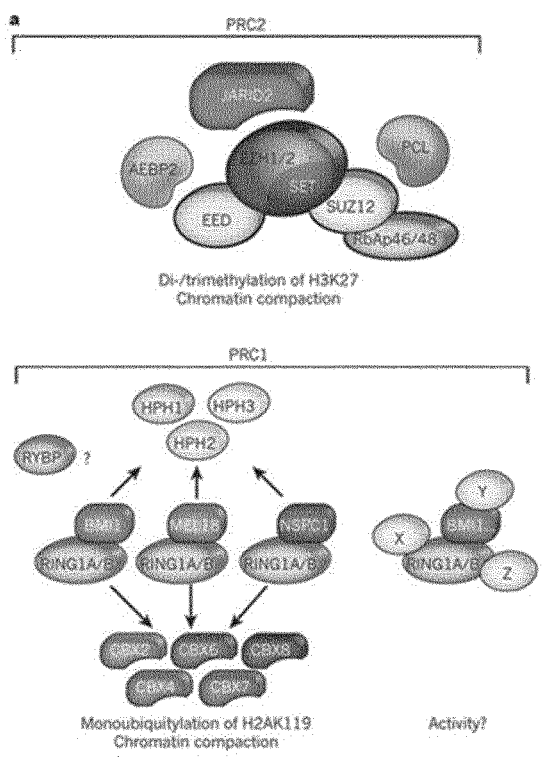

FIG. 31. Schematic representation of the molecular composition of Prc1 and Prc2.

DETAILED DESCRIPTION OF THE INVENTION

Material and Methods

Murine Models
Mouse Lines
CCM1$^{fl/fl}$ and CCM3$^{fl/fl}$ Mice

CCM1$^{fl/fl}$ and CCM3$^{fl/fl}$ mice have exons 4-5 of the ccm1 and the ccm3 gene flanked by loxP sites (produced by Artemis Taconis). Deletion of exons 4-5 by Cre-mediated recombination produces loss-of-function alleles.
VECPAC/CCM1$^{fl/fl}$ and VECPAC/CCM3$^{fl/fl}$ Mice CCM1$^{fl/fl}$ and CCM3$^{fl/fl}$ mice were bred with vascular endothelial cadherin-CreERT2 (VECPAC) mice to obtain VECPAC/CCM1$^{fl/fl}$ and VECPAC/CCM3$^{fl/fl}$ mice.

These mice express cre-recombinase fused to the mutated form of the human estrogen receptor (ERT2). ERT2 is activated by tamoxifen, at low levels, but not by the endogenous estrogen. This fusion protein is expressed under vascular endothelial cadherin (Cdh5) promoter, therefore only in endothelial cells.

Upon tamoxifen injection (or its active metabolite 4-hydroxy-tamoxifen (4-OHT)), cre-recombinase-ERT2 fusion protein is released from heat shock proteins (hsp) and moves to the nucleus where cre-recombinase recombines loxP sites.
Mouse Endothelial Cell-Specific Recombination with Tamoxifen VECPAC/CCM3$^{fl/fl}$ and VECPAC/CCM3$^{fl/fl}$/R26-Confetti mice were treated with tamoxifen (Sigma) to specifically induce recombination of floxed-genes in endothelial cells.

Tamoxifen was first dissolved in pre-warmed (37-40° C.) ethanol to a final concentration of 100 mg/mL. Then pre-warmed corn oil was slowly added to a final concentration of 10 mg/mL.

Tamoxifen (10 mg/mL) was aliquoted and stored in the dark at −20° C.

The day of injection an aliquot of tamoxifen was diluted to a final concentration of 2 mg/ml in corn oil and 50 μL of the solution was injected intragastric into each mouse.
Mouse Treatment with PTC209 and UNC1999

Starting from the day after tamoxifen injection, cre-positive VECPAC/CCM3$^{fl/fl}$ mice received daily an intragastric injection of: PTC209 (Tocris Cat. No. 5191 10 ug/g body weight), UNC1999 (Sigma-Aldrich SML0778 25 ug/g body weight) or a combination of the two. The two drugs were first dissolved in dimethyl sulfoxide (DMSO) and then in 50 μL of corn oil. The control mice were treated with the same amount of DMSO, dissolved in 50 μL of corn oil. The animals were sacrificed for analysis at 8 days postnatal (dpn).
Mouse Genotyping To prepare DNA for genotyping, mice's tails were lysed in Buffer G 10% (Stock 10×: 2.19 g Ammonium Sulfate; 35uLE5uLateum@Sulfate 2.13, 13.4 uL EDTA 0.5M pH 8, 49 uL Tris HCl 1M pH 8.8 in water) 20% TX-100, 2.5% proteinase K in water overnight in agitation at 2000 rpm at 56° C.

Lysed tails were then heated at 95° C. for 5 minutes before being genotyped.

The following probes were used for mouse genotyping:
Two primers were used to distinguish wild-type ccm1 allele from the floxed one.

5' CACTTGTCTAATACCAACAAGGG 3' (SEQ ID No. 1)

5' CCTATCTACATCTCCCTATTGC 3' (SEQ ID No. 2)

Two primers were used to distinguish wild-type ccm3 allele from the floxed one.

5' GAT AGG AAT TAT TAC TGC CCT TCC 3' (SEQ ID No. 3)

5' GAC AAG AAA GCA CTG TTG ACC 3' (SEQ ID No. 4)

Three primers were used to distinguish wilt-type allele from the allele with R26-confetti.

5' GAATTAATTCCGGTATAACTTCG 3' (SEQ ID No. 5)

5' AAAGTCGCTCTGAGTTGTTAT 3' (SEQ ID No. 6)

5' CCAGATGACTACCTATCCTC 3' (SEQ ID No. 7)

The first primer (forward) binds the DNA upstream the R26-Confetti cassette and is able to pair with the other two. The second primer binds the DNA on the wild type allele, while the third binds the R26-Confetti cassette.
Immunofluorescence of Brain Immediately after dissection, brains from pups were fixed in 4% paraformaldehyde (PFA) at 4° C. overnight. Fixed brains were embedded in 4% low-melting-point agarose and sectioned (100 um) along the sagittal axis using a vibratome (1000 Plus, The Vibratome Company, St. Louis, MO, US).

Brain sections were stained as floating samples in 6- or 12-wells plates. They were blocked 1 hour at room temperature (RT) in 0.3% Triton X-100, 5% donkey serum, 1% Bovine Serum Albumin (BSA) in Phosphate-Buffered Saline (PBS). The samples were incubated overnight at 4° C. with the primary antibodies diluted in the same solution that was used for blocking. Several washing in 0.1% Triton X-100 in PBS were performed and then the secondary antibodies were added for 4 hours at RT in 0.3% Triton X-100, 1% BSA in PBS.

After secondary antibody incubation further washes in PBS were performed, followed by a post-fixation step with 4% paraformaldehyde for 5 minutes at RT. Further washes in PBS were done after post-fixation step. The brain sections were mounted in Vectashield with 4',6-diamidino-2-phenylindole (DAPI).

DAPI is a fluorescent stain that binds strongly to A-T rich regions in DNA. It is used to stain nuclei of fixed or living cells. The coverslip was fixed with nail polish.

Quantification of Lesions

After staining for immunofluorescence microscopy with Ib4 and SCA1 antibody, brain sections were examined under confocal microscopy (10×). The total number of lesions was calculated by summing all types of lesions per brain. The area of lesions per brain was also quantified. The number and area of lesions were counted blindly respect to treatment.

Sterility Methods

All in vitro procedures were performed under laminar flow hood. Virus infected cultures were handled under class II laminar flow hood. Cells were cultured at 37° C. in a humidified atmosphere with 5% $CO_2$.

Cell Cultures

Preparation of Primary Cell Cultures

Wild type, CCM1 knock-out and CCM3 knock-out Endothelia Cells (ECs) were used as in vitro model of CCM. ECs were obtained from lungs or brain of respective floxed mouse strain.

Freshly Isolated Lung ECs

Lung-derived ECs were isolated from lungs of two months-old $CCM1^{fl/fl}$ mice and $CCM3^{fl/fl}$ mice upon organ dissection and disaggregation. Disaggregation of tissue was performed with collagenase A (1.5 mg/ml; Roche) and DNase (25 ug/mL; Roche) in DMEM (Life Technology) for 1 hour at 37° C. with occasionally shacking and pipetting.

Freshly Isolated Brain ECs

Brain-derived ECs were isolated from VECPAC/$CCM3^{fl/fl}$/R26-Confetti. Brains were processed with two different MilteniyiBiotec kits depending on the age at which the mice were sacrificed: "Adult Brain Dissociation Kit", for up to 7-days old mice, or "Neural Tissue Dissociation Kit" for less than 7-days old mice. All protocols and data sheet are available at www.milteniyibiotec.com.

For both kits, brains were isolated from mice in sterile condition and immediately place in HBSS without Calcium and Magnesium (Euroclone) plus penicillin/streptomycin 100 units/l (Microtech). It is important to maintain organs on ice.

Under sterile hood brains were then incubated in a sterile C-Tube with 1950 uL of Enzyme Mix 1 (composed by 10 uL of Enzyme P plus 1940 uL of Buffer X, every 400 mg of starting tissue material) plus 30 uL of Enzyme Mix 2 (composed by 20 uL of Buffer Y plus 10 uL of Enzyme A, every 400 mg of starting tissue material) and processed in the gentleMACS Dissociator. For Adult Brain the 37C_ABDK program was selected, while for Brain of pups with less than seven days the 37C_NTDK_1 program was selected. The gentleMACS Dissociator processes brains at 37° C. with mechanical lysis.

After dissociation of tissues, each sample was resuspended with a p1000 pipet and the cell suspension was incubated with CD45 MicroBeads 15 minutes at 4° C. following the protocol from MilteniyiBiotec. CD45 positive cells were negatively selected trough magnetic field on a MACS Separator with LD columns. Briefly, MicroBeads conjugated to monoclonal anti-mouse CD45 antibody bind to CD45 (leukocyte common antigen) positive cells. Passing through the LD column, placed on a MACS Separator, the CD45 positive cells attach to the column. By collecting the flow-through only CD45 negative cells were selected and the positive ones were depleted. A second incubation with MicroBeads conjugated to monoclonal anti-mouse CD31 antibody was necessary to increase the purity of the starting culture. CD31 is a typical marker of endothelial cells, is therefor important to select the CD31 positive cells. By applying cells incubated with CD31 MicroBeads on a MS column, was possible to discard the flow-through and collect only cells that remain attach to the column by flushing out the magnetically labelled cells (CD31 positive endothelial cells).

For "Adult Brain Dissociation Kit" a further step was required called Debris Removal. By applying 900 uL of Debris Removal Solution every 3100 uL of PBS to the cell's suspension derived from dissociation of tissue, was possible to eliminate cell debris from viable cells and so increase the purity of each sample. Briefly, Debris Removal Solution is a ready-to-use gradient reagent that allows the formation of three phases because of the different density between Debris Removal Solution and the overlay of PBS. After centrifugation (10 minutes, 3000 g, 4° C.) lightweight particles (cell debris) remain in between PBS and Debris Removal Solution (inter-phase). The heaviest living cells in contrast lie on the bottom. By removing the two top phases completely is possible to avoid cell debris from each sample.

Immortalisation of Primary Cell Cultures with Polyoma Middle T

Cell immortalization was performed 24 to 48 hours after isolation and seeding in 48-wells plates of freshly isolated ECs. The cells were incubated with $10^5$ neomycin-resistant colony-forming units of the retrovirus vector N-TKmT in 500 µL of complete medium per well in the presence of 8 g/mL polybrene (Sigma). N-TKmT retrovirus vector expresses polyomavirus middle T antigen, which is able to immortalize cells by mimicking an activated growth factor receptor (MT associates with signalling proteins at different sites in its maturation pathway. Ex. MT binds to PP2A in the cytoplasm and to c-Src at the Endoplasmic Reticulum). The virus-containing medium was replaced 12 hours after incubation with complete medium. PmT-infected cells were maintained in culture until a monolayer of Endothelial Cells is visible. In previous studies, it was observed that PmT specifically immortalizes endothelial cells and not any other cell types. This allows pure endothelial cell lines to be obtained even if starting from a mixed population. The other non-endothelial cells tended to be lost within 2 or 3 passages.

Culture Condition

Freshly Isolated ECs.

Freshly isolated ECs were cultured in sterile condition on collagen I-coated 48-wells plates. Complete medium for freshly isolated cells was composed by: MCDB 131 (Life Technology) with 20% North America Fetal Bovine Serum (Sigma), glutamine 2 mM (Microtech), penicillin/streptomycin 100 units/L (Microtech), heparin 100 ug/mL (from porcine intestinal mucosa; Sigma) and EC Growth Supplement 100 ug/mL (Sigma). Freshly isolated ECs grow up to confluence and are passaged 1:2. Cells were cultured in sterile conditions at 37° C. in a humidified atmosphere with 5% $CO_2$.

Immortalized ECs.

Once immortalized ECs were cultured in sterile condition in flasks coated with 0.1% gelatin. Complete medium for immortalized cells was composed by: MCDB 131 (Life Technology) with 10% North America Fetal Bovine Serum (Sigma), glutamine 2 mM (Microtech), penicillin/streptomycin 100 units/L (Microtech), heparin 40 ug/mL (from porcine intestinal mucosa; Sigma) and EC Growth Supplement 20 ug/mL (Sigma). Immortalized ECs grow up to confluence and are passaged 1:3. All cells were cultured in sterile conditions at 37° C. in a humidified atmosphere with 5% $CO_2$.

In Vitro Recombination of loxP-Flanked Genes

Recombination of the loxP-flanked genes was induced by treating cells the day after the first splitting (1:2) with 100 ug/mL TAT-Cre-recombinase for 60 minutes in HyClone™ ADCF-MAb medium (GE Healthcare) without serum followed by 100 uM chloroquine for 30 minutes. The cells were washed with HyClone™ ADCF-MAb medium and cultured with complete medium.

If the mice were Cre-positive another approach was to treat cells with 4OH-tamoxifen 1 uM in DMSO for three days to induce recombination.

After recombination cells that derived from $CCM1^{fl/fl}$ mice lose ccm1 gene while cells that derived from $CCM3^{fl/fl}$ mice lose ccm3 gene.

Cells isolated from VECPAC/$CCM3^{fl/fl}$/R26-Confetti mice, after recombination lose ccm3 gene and acquire, in a stochastic way, one of the four fluorescent proteins that are present in the Brainbow2.1 cassette. With R26-Confetti reporter is possible to follow indirectly the level of recombination of the ccm3 gene.

Cells Treatment with PTC209 and UNC1999

Cells were seeded $6.3 \times 10^4$ cells/$cm^2$. The day after, PTC209 and UNC1999 were added to the confluent cells. Drugs were left for one or three days depending on the aim of the experiment. Final concentrations used for the two drugs were: 1 uM PTC209 and 5 uM UNC1999.

Drugs were dissolved in DMSO at 1000× concentration in order to keep final concentration of DMSO below 1%. Control was treated with DMSO at the same amount of the two drugs.

Immunofluorescence on Cell Cultures

To perform immunofluorescence on cells, first is required the preparation of sterile glass slides coated with cross-linked gelatin.

Glass slides (13 mm diameter) were cleaned in ethanol and sterilized with autoclave. Once ready, glass slides were placed in a 24-well (one glass per well) and coated with 0.5% gelatin (1 hour at RT). 2% glutaraldehyde solution was then used to crosslink the gelatin (15 minutes at RT). Glutaraldehyde was replaced with 70% ethanol for 30 minutes to sterilize the glass slides. Ethanol was replaced and several washing in PBS were performed to avoid ethanol contamination. Glass slides were then left overnight in glycin 2 mM. Several washing in PBS were made before use.

Cells were seeded on the glass slides previously prepared.

For immunofluorescence, cells were fixed in three different ways: with 4% PAF in PBS (followed by permeabilization with 0.5% Triton X-100 for 5 minutes); with 1% PAF in triethanolamine pH 7.5, containing 0.1% Triton X-100 and 0.1% NP-40 for 10 minutes at RT or in methanol for 5 minutes at 20° C. Blocking (1 hour, RT) were performed in PBS containing 2% BSA and 5% donkey serum. Primary (overnight, 4° C.) and secondary (50 minutes, RT) antibodies were incubated in PBS with 2% BSA.

Cells-covered glass slides were mounted in Vectashield containing DAPI and fixed with nail polish on a microscope slide.

Western Blot Analysis

Confluent cells were lysed with boiling modified Laemi sample Buffer (2% SDS, 20% glycerol, and 125 mM Tris-HCl, pH 6.8). Lysates were incubated for 10 minutes at 100° C. to allow proteins denaturation. Protein concentration was estimated using the BCA Protein Assay Kit (Pierce). Equal amount of proteins was loaded on a gel, separated by SDS-PAGE and transferred to a Protran Nitrocellulose Membrane (Whatman) 0.2 um pores. The membranes were blocked for 1 hour at RT in Tris Buffered Saline (TBS: NaCl 150 mM, Tris-HCl 10 mM pH 7.4) plus 0.1% Tween-20 containing 5% BSA or milk. The membranes were incubated with primary antibodies diluted in TBST (TBS plus 0.1% Tween-20) containing 5% of either BSA or milk overnight at 4° C. Next, membranes were rinsed three times with TBST for 5 minutes each and incubated for 45 minutes at RT with HRP-linked secondary antibodies diluted in TBST containing 5% BSA/milk. Membranes were rinsed three times with TBST for 5 minutes each and specific bindings were detected by enhanced chemiluminescence (ECL) system (Amersham Bioscience) using ChemiDoc XRS gel imaging system (Bio-Rad).

ECL detention is based on HRP/Hydrogen Peroxide catalyzed oxidation of luminol in alkaline conditions. Immediately following oxidation, the luminol is in an excited state which then decays to ground state via a light-emitting pathway. Enhanced chemiluminescence is achieved by performing the oxidation of luminol by the HRP in the presence of chemical enhancers such as phenols. This has the effect of increasing the light output approximately 1000 fold and extending the time of light emission.

The molecular mass of proteins was estimated relatively to the electrophoretic mobility of co-transferred pre-stained protein marker, Broad Range (Cell Signaling Technology).

Antibodies

For immunofluorescence and western blotting, the following antibodies were used: Bmi1 mouse (sc-8906, Santa Cruz); Ezh2 mouse (NCL-L-EZH2, Leica); VE-cadherin mouse (sc-6458, Santa Cruz); PECAM1 hamster (MAB1398Z, Millipore); PECAM1 rat (553370, BD); PECAM1 rabbit (ab28364, Abcam); mKLF4 goat (AF3158, R&D); FSP1 rabbit (07-2274, Millipore); ID1 rabbit (BCH-1/37-2, BIOCHECK); SCA1 rat (ab51317, Abcam); Phospho-SMAD3 (9520, Cell Signaling); pSMAD3 (ab52903, Abcam); SMAD3 rabbit (9523S, Cell Signalling); Phospho-SMAD1/5 rabbit (9516, Cell Signaling); SMAD1 rabbit (9644, Cell Signaling); GFP rabbit (2956, Cell Signaling); HA-tag mouse (TA180128S, Origene); Tubulin mouse (T9026, Sigma); Vinculin mouse (V9264, Sigma); LEF1 rabbit (2230S, Cell Signaling); Isolectin IB4 Biotin Conjugates (Vector Laboratories); Streptavidin 647 (Molecular Probes); Horseradish peroxidase (HRP)-linked anti-mouse, anti-rat, anti-rabbit (Cell Signaling); HRP-linked anti-goat (Promega). ALEXA FLUOR 488, 555 and 647 donkey secondary antibodies were from Life Technologies.

RT-qPCR

RNA extraction was performed both with (A) RNeasy kits (Promega) or (B) RNAeasy Mini Kit (QIAGEN). The latter allows also the extraction of proteins from the same sample. The RNA (500 ng) was reverse transcribed with random hexamers (High Capacity cDNA Archive kits; Applied Biosystems) in a final volume of 30 uL. Reaction were made with a thermocycler (Eppendorf) 10 min at 25° C. followed by 2 hours at 37° C. cDNA (5 ng) was amplified in triplicate in a reaction volume of 15 uL using TaqMan Gene Expression Assays (Applied Biosystems) in a ABI/Prism 7900 HT using a pre PCR step of 10 min at 95° C., followed by 40 cycles of 15 seconds at 95° C. and 60 seconds at 60° C. For each sample, the expression level was determined with the comparative threshold cycle (Ct) method, and normalized to the housekeeping genes encoding 18S, glyceraldehyde-3-phosphate dehydrogenase (GAPDH) and hypoxanthine-guanine phosphoribosyltransferase (hprt1). Ct or threshold cycle, represents the PCR cycle at which an increase in reporter fluorescence above a base-line signal can first be detect.

DCt of threshold cycle, represents the $Ct_s$ of the gene of interest normalized on the geometric mean of the three housekeeping genes. The amount of target gene, normalized to an endogenous reference and relative to a calibrator is given by the following formula: Fold change=$2^{(-DDCt)}$ where DDCt is the difference between the DCt of the gene of interest and the DCt of the endogenous control.

(A) RNeasy Kits of Promega allows the extraction of RNA with minimal lysate handling before automated purification on the Maxwell RSC Instrument (Cat. #AS4500). First cells are lysed in a 1-Thioglycerol/Homogenization Solution. The 1-Thioglycerol is a reducing agent that will irreversibly denature RNAses by reducing disulfide bonds and destroying the native conformation required for enzyme functionality. Than the same amount of Lysis Buffer is added to the cell pellet dissolved in the 1-Thioglycerol/Homogenisation and the total volume is placed on a Maxwell RSC Cartridge. In the Maxwell RSC instrument, the sample is mixed by rapid up-and-down movements of a single-use plunger. A MagneSil Paramagnetic Particles which are captured after a magnetic rod insert down the middle of the plunger, binds the nucleic acid which are purified through a series of capture and release washes. The purified nucleic acids are released in elution tube filled with 50 µL of water.

B) RNAeasy Mini Kit (QIAGEN) provides fast purification of high-quality RNA from cells. RNA is isolated on a silica membrane in trusted RNeasy spin columns, which have binding capacities of 100 ug of RNA.

To obtain from the same sample both RNA and proteins this kit was used.

Samples are first lysed with a RTL Buffer, which contains a high concentration of guanidine isothiocycanate, which supports the binding of RNA to the silica membrane (β-mercaptoethanol is added to Buffer RLT before use to effectively inactivate RNAses in the lysate). The lysate is pipetted onto a QIAsheder spin column to improve the efficiency of the lysate. Ethanol is added to the lysate to provide ideal binding conditions. The lysate is then loaded onto the RNeasy silica membrane. RNA binds (up to 100 µg capacity), and all contaminants are efficiently washed away with Buffer RW1 which contains a guanidine salt, as well as ethanol, and is used as a stringent washing buffer that efficiently removes biomolecules such as carbohydrates, proteins, fatty acids etc., that are non-specifically bound to the silica membrane. At the same time, RNA molecules larger than 200 bases remain bound to the column. Traces of salt, which are still on the column due to buffers used earlier in the protocol are removed with Buffer RPE. Ethanol is added by the user just before using the kit for the first time.

After the step on RNeasy silica membrane is possible to extract proteins from the Buffer RLT lysates by adding 4 volumes of ice-cold acetone to the flow-through and by incubating them for 30 min in ice.

The solubility of protein depends on, among other things, the dielectric constant of the solution. In general, solvent molecules with large dielectric constants can stabilize the interaction between themselves and protein molecules and promote the dissolution of protein. On the other hand, organic solvents with small dielectric constants, e.g. acetone and methanol, discourage the dispersion of protein molecules in the media. Thus, the solubility of proteins can be lowered and precipitation can be induced by lowering the effective dielectric constant of the media. This is commonly achieved by adding a water-soluble solvent such as acetone to an aqueous solution of protein. Doing the process at low temperature is important to avoid the denaturing effect of the acetone.

Production of Cell Lines Expressing Green Fluorescent Protein and ANLef-BCTA

Plasmids Used:

pLVX-AcGFP1-N1 (FIG. 29)

Once integrated in DNA of the host this plasmid is responsible for the expression of the Green Fluorescent Protein (GFP), easily detectable by fluorescence microscopy.

LefΔN-β-catΔC (FIG. 30)

LefΔN-β-catΔC is a constitutively active mutant made by the fusion of the transcription factor LEF1 and the transactivation domain of the b-catenin. This is a constitutively active mutant that activate gene target transcription without playing any role at the membrane. Human influenza hemagglutinin (HA) is a surface glycoprotein required for the infectivity of the human influenza virus. The HA tag is derived from the HA-molecule corresponding to amino acids 98-106. It has been extensively used as a general epitope tag in expression vectors. The HA-tag domain allows detection by Western Blot analysis or by immuno-fluorescence of the entire fusion protein in order to study the expression level of the inventors' exogenous construct.

Transformation of DH5α

DH5α bacteria were used to amplify plasmids. This strain of *E. Coli* is not pathogenic and was developed for laboratory use. This strain also has the ability to accept plasmid insertion exceptionally well.

DH5α were incubated on ice for 30 minutes with the plasmid. To produce a thermic shock, which facilitates the entrance of the plasmid into the bacterial membrane, the sample (DH5α plus plasmid) was incubated at 42 C for 20 minutes and immediately replaced on ice for 2 minutes.

After thermic shock the bacteria were incubated for one hour in agitation at 225 rpm in Luria-Bertani (LB) medium (1% NaCl, 1% Tryptone, 0.5% Yeast Extract in water) at 37° C. After 1 hour of incubation bacteria were plated on a petri coated with solid LB plus ampicillin (final concentration 100 ug/ml) to select only bacteria containing the plasmid. Different dilutions were made in order to obtain visibly single colonies of transformed bacteria. Petri were left overnight at 37° C. in the incubator.

Purification of Plasmid DNA with MaxiPrep Kit (QIAGEN)

To purify plasmid DNA one single colony was picked from the petri with a top and placed in a 50 mL tube filled with 5 mL of LB medium containing ampicillin (100 ug/mL).

The tubes were incubated 8 hours at 37° C. vigorous shaking (approx. 300 rpm). The starter cultures were diluted 1/1000 into selective LB medium and were grown at 37° C. for 12-16 hours with vigorous shaking (approx. 300 rpm). The bacteria were harvest by centrifugation at 6000 g for 15 minutes at 4° C., and the pellet was resuspended in Buffer P1 (isotonic resuspension buffer: 50 mM Tris-HCl pH 8.0 to maintain the DNA in his double-strands conformation; 10 mM EDTA pH 8.0 to sequestrate $Mg^{2+}$ ions that could act as co-enzyme and activate DNases; and moreover EDTA sequestrates $Ca^{2+}$ ions and so that allows the leakage of the membrane and blocks the lysozyme responsible for impurity on the DNA if It is used for more than 2 minutes) plus RNase A (final concentration 100 ug/mL) provided by the kit. To lyse bacteria, Buffer P2 (alkaline lysis buffer: 200 mM NaOH, 1% SDS w/v) was added to the suspension. SDS denatures proteins and creates hole in the membrane and sodium hydroxide breaks the bacterial wall and denatures the chromosomal DNA though linearization and separation but do not affect plasmid DNA. The tube containing the solution was vigorously inverted 4-6 times and incubated at RT for 5 minutes. Chilled Buffer P3 (neutralisation buffer: 3.0 M potassium acetate, pH 5.5) was added to the solution and the preparation was vigorously inverted 4-6 times and incubated in ice for 20 minutes. The neutralisation phase brings the pH back to the physiological value and so that allows the re-naturation of the superimposed plasmid but not the genomic DNA due to its large size. Potassium acetate neutralizes NaOH. The sample was than centrifuged at 20000 g for 30 minutes at 4° C. In this way the genomic DNA precipitates and the supernatant containing plasmid could be re-centrifuged 20000 g for 15 minutes at 4° C. to increase the purity.

To concentrate the plasmid DNA, a silica gel membrane column was used, based on selective absorption: first the QUIAGEN-tip 500 column was equilibrated with Buffer QBT (750 mM NaCl, 50 mM MOPS pH 7.0, 15% isopropanol v/v, 0.15% Triton X-100); than supernatant containing plasmid was applied to the column and by flow gravity It enters the resin; 2 washes with Buffer QC (1.0M NaCl, 50 mM MOPS pH 7.0, 15% isopropanol v/v) were used to remove contaminants; the DNA was eluted with Buffer QF (1.25M NaCl, 50 mM Tris-HCl pH 8.5, 15% isopropanol v/v) and collected in a 15 ml tube.

To precipitate the DNA isopropanol was added to the eluted DNA and the sample was mixed and immediately centrifuged at 15000 g for 30 minutes at 4° C. The pellet was then washed with 70% ethanol and centrifuged at 15000 g for 10 minutes. The pellet was air-dry 5-10 minutes and re-dissolved in a suitable volume of buffer (TE buffer pH 8.0).

Transfection—Lentivirus Mediated Gene Delivery HEK293T

For transfection Human Embryonic kidney cells 293 (HEK293T) cells were used. HEK293T was generated by stable transfection of the HEK293 cell line with a plasmid encoding a temperature-sensitive mutant of the SV40 large T antigen. 293T cells are very efficiently transfectable with DNA. Due to the expression of SV40 large T antigen, transfected plasmid DNAs that carry the SV40 origin of replication can replicate in 293T and will transiently maintain a high copy number; this can greatly increase the amount of recombinant protein or retrovirus that can be produced from the cells.

Packaging Plasmids

To increase the safety of lentivirus, the components necessary for virus production are split across multiple plasmids:
  ENV (VSV-G), envelope plasmid.
  Gag & pol, packaging plasmid.
  REV, nuclear localisation plasmid.

Co-transfection of HEK293T cells was done following this protocol: one day before transfection $7.5\times10^6$ cells/plate were seeded in a 15 cm plate. 22 mL of complete DMEM High Glucose w/o L-Glutamine (Lonza) was used. 2 hours before transfection, medium was changed to the cells (22 mL).

For the transfection were used: 7 ug ENV (VSV-G), 12.5 ug pMDL (gag & pol), 6.25 ug REV, 32 ug Gene Transfer, up to 1094 ul 0.1×TE sterile, 156 ul $CaCl_2$) 2M.

A mix was prepared and left 5 minutes at RT. While mixing vigorously 1.25 mL HBS 2× was added. 2.5 mL of final volume was then added dropwise to the medium of the HEK293T and left over night at 37° C.

Virus Concentration

The day after, the medium was changed with 18 mL of medium. 30 hours post transfection the medium was taken and filtered through a 0.45 μm PDVF Millipore filter to eliminate cellular debris. The supernatant was than transferred to a sterile vessel and 1 volume of cold PEG-it™ Virus Precipitation Solution (System Bioscience) was added every 4 volume of supernatant (PEG-it is a 5× solution) and incubated overnight at 4° C.

The day after, supernatant/PEG-it™ mixture was centrifuged at 1500 g for 30 minutes at 4° C. All traces of fluid were removed by aspiration, taking care not to disturb the pellet. The pellet was than re-dissolved in a suitable volume of PBS and immediately aliquot and frozen at −80° C. until ready for use.

Infection

One day before infection, 300.000 cells/well were seeded in a 6-wells plate in complete medium as described before.

The day after 40 uL per well of the concentrated virus was added to the cells medium and leaved overnight at 37° C. The day after infection medium of the infected cells was changed and the cells were cultured in complete medium.

Following cells line were obtained:
  Lung immortalize CCM1 wild-type ECs expressing GFP
  Lung immortalize CCM1 wild-type ECs expressing dtTomato
  Lung immortalize CCM1 knock-out ECs expressing GFP
  Lung immortalize CCM1 knock-out ECs expressing dtTomato
  Lung immortalize CCM3 wild-type ECs expressing GFP
  Lung immortalize CCM3 wild-type ECs expressing dtTomato
  Lung immortalize CCM3 knock-out ECs expressing GFP
  Lung immortalize CCM3 knock-out ECs expressing dtTomato
  Lung immortalize CCM3 wild-type ECs expressing LefΔN-β-catΔC Statistical Analysis Two-tailed, unpaired t-test was used to determined statistical significance. The significance level was set at $p<0.05$.

For western blot analysis, relative vinculin or tubulin intensity was used as loading control while for real time analysis was used three housekeeping genes encoding for: 18S, glyceraldehyde-3-phosphate dehydrogenase (GAPDH) and hypoxanthine-guanine phosphoribosyltransferase (hprt1).

EXAMPLES

Example 1: Bmi1 was Upregulated in CCM3 Knock Out Endothelial Cells, Both In Vitro e In Vivo Previous work demonstrated that Bmi1 was upregulated in a number of human malignancies (Glinsky, Berezovska, & Glinskii, 2005) (Guo et al., 2007) (Rizo et al., 2009) (Radulović, de Haan, & Klauke, 2013) (Kreso et al., 2013). Moreover, Bmi1 overexpression in immortalized and transformed breast epithelial cells induced epithelial-to-mesenchymal transition with an increase in their sphere-forming efficiency and expression of stemness-related genes (Paranjape et al., 2014). Epithelial-to-mesenchymal transition shares molecular mechanisms with endothelial-to-mesenchymal transition, which has been demonstrated to be an underlying mechanism of CCM (Maddaluno et al., 2013). Because breast cancer cells, undergoing EMT overexpress Bm1, the inventors wondered whether CCM3 knockout cells, undergoing EndMT, overexpressed Bmi1.

To check Bmi1 expression level in the inventors' models of CCM, western blot and immunofluorescence analysis were done on wild type and CCM3 knock out cells.

CCM3 knock out cells were immortalized lung endothelial cells derived from VECPAC/CCM3$^{fl/fl}$ mice, treated with TAT-Cre recombinase. TAT-Cre recombinase treatment induced deletion of Ccm3 floxed-gene. As control the same cell line without TAT-Cre treatment were used.

Figure 1:
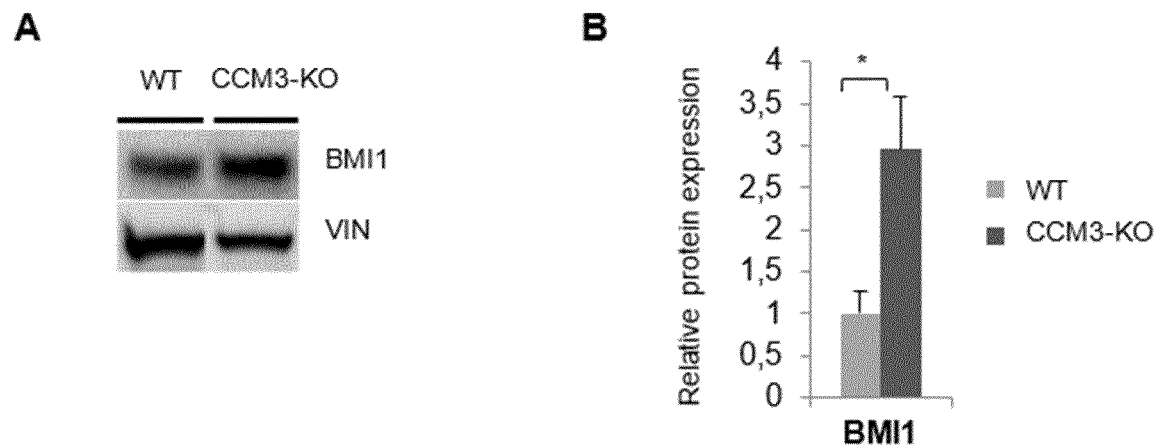
FIG. 1. Bmi1 was upregulated in CCM3 knockout cells compare to wild type cells.

Western blot analysis (FIG. 1A) and the relative quantification (FIG. 1B) showed upregulation of Bmi1 protein expression level in CCM3 knock out cells compared to wild type cells.

Also immunofluorescence analysis, performed on the same cell lines, showed upregulation of nuclear Bmi1 in CCM3 knock out cells compared to wild type cells (FIG. 2).

Subsequently, PTC209, a low molecular weight compound used for the first time by Kreso et al. to inhibit Bmi1 in cancer initiating cells of colorectal cancer (Kreso et al., 2013), was used to inhibit Bmi1 in the inventors' model.

In particular, wild type and CCM3 knockout cells were treated starting from the day after seeding with PTC209. In parallel, as control, both wild type and CCM3 knock out cells were treated with a volume of DMSO equal to the volume of DMSO in which PTC209 was previously dissolved to rich the optimal concentration.

Cells were lysed for western blot analysis after 24 hours of treatment.

Data (FIGS. 3A and B) confirmed the upregulation of Bmi1 in CCM3 knock out cells compared to wild type cells and moreover showed a downregulation of Bmi1 upon PTC209 treatment both in wild type and in CCM3 knock out cells. These results confirmed the efficiency of PTC209 compound in inhibiting Bmi1, as already showed by Kreso et al. (Kreso et al., 2013)

Example 2: Bmi1 Inhibition Reduced EndMT Markers in CCM3 Knockout Endothelial Cells To study the correlation between Bmi1 and the EndMT observed in CCM models (Maddaluno et al., 2013), the inventors investigated the effect of Bmi1 inhibition on expression of EndMT markers, such as Klf4, Sca1 and Fsp1.

Wild type and CCM3 knock out cells were treated with either PTC209 or DMSO starting from the day after seeding, when cells were confluent. For this experiment cells were lysed for western blot and real-time analysis after 72 hours of treatment to check a long-term effect of PTC209.

Western blot analysis (FIGS. 4A and B) showed a strong upregulation of protein expression of EndMT markers in CCM3 knock out cells compared to wild type cells, as already published by Bravi et al. (Bravi et al., 2015).

Moreover, western blot analysis showed that EndMT markers protein expressions were strongly downregulated in CCM3 knock out cells treated with PTC209, compared to cells treated with DMSO (FIG. 4B). Moreover, levels of Klf4 and Sca1 in CCM3 knock out cells treated with PTC209 were comparable with the levels expressed by wild type cells (FIG. 4B).

The inhibitory effect of PTC209 on EndMT markers was confirmed also by real time analysis. As shown in FIG. 5, Klf4 and Fsp1 were significantly upregulated in CCM3 knock out cells respect to wild type cells. This was not valid for Sca1 transcript, which was downregulated in CCM3 knock out cells respect to wild type. Despite this, western blot analysis (FIG. 4) clearly showed that Sca1 was upregulated at the protein level. This could be explained by the fact that high protein level could induce a negative feedback loop at the transcript level.

Anyhow also by real time analysis Klf4, Sca1 and Fsp1 are downregulated upon Bmi1 inhibition in CCM3 knock out cells (FIG. 5), suggesting an involvement of Bmi1 in the regulation of EndMT markers expression.

Interestingly, Klf4 showed a different response to PTC209 compared to Sca1 and Fsp1; in particular, in wild type conditions Klf4 was not affected by the Bmi1 inhibitor, while, the up-regulation induced by CCM3 deletion were completely rescued. This was observed in western blot (FIG. 4) as well as real-time (FIG. 5) analysis. This suggests a possible different mechanism of regulation of Klf4 compared to Sca1 and Fsp1. Likely Bmi1 acts downstream of Klf4 in physiological condition, and can play a role in its upregulation upon CCM3 loss.

Considering that all these experiments were done on immortalized lung endothelial cells, there was the necessity to confirm these data also on fleshly isolated brain endothelial cells. Indeed, brain endothelial cells represents an in vitro model that better mimics the environment in which the lesions are formed both in mouse models of CCM and in human patients.

In order to generate a brain endothelial cell line, VECPAC/CCM3$^{fl/fl}$ mice were sacrificed, and the derived isolated brain endothelial cells (CCM3$^{fl/fl}$) were cultured. To obtain a CCM3 knock out cell lines, CCM3$^{fl/fl}$ cells were recombined in vitro using TAT-Cre recombinase. As control (wild type) the same CCM3$^{fl/fl}$ cells were not treated.

As shown in FIG. 6A, upon TAT-Cre treatment, Ccm3 transcript level was almost completely downregulated (decreased of 83±1.9% in CCM3$^{fl/fl}$ cells treated with TAT-Cre compare to wild type cells).

To test inhibitory effect of PTC209 on freshly isolated brain endothelial cells, wild type and CCM3 knock out cells (CCM3$^{fl/fl}$+TAT-Cre) were treated with PTC209, the day after recombination, with the same experimental condition used on immortalized lung endothelial cells (FIG. 6B).

Results showed that upon Ccm3 deletion using TAT-Cre recombinase treatment, also freshly isolated brain endothelial cells showed upregulation of EndMT markers, as already published (Bravi et al., 2015) and thus confirming the validity of the inventors' cell line. Moreover, Bmi1 inhibition strongly reduced Sca1 and Fsp1 expression in CCM3 knock out cells (CCM3$^{fl/fl}$+TAT-Cre). Klf4 was not downregulated upon Bmi1 inhibition probably due to the timing of the experiment. Klf4 has been shown to be upregulated three days after recombination of Ccm3 genes in vitro (Bravi et al., 2015). Indeed, starting treatment one day after recombination was probably to early to see a downregulation of Klf4.

Taken together, these data indicated that freshly isolated brain endothelial cells CCM3 knock out upregulated EndMT markers and responded to PTC209 treatment in the same way as immortalized lung endothelial cells, suggesting that immortalized lung endothelial cells were a good and simpler model to investigate the effect of Bmi1 inhibition in vitro.

Example 3: Bmi1 Inhibition Did not Rescue Junctional Disorganisation in CCM3 Knockout Cells Beside the upregulation of mesenchymal markers, another crucial effect of CCM3 deletion is adherens junctions disorganization.

Indeed, in a previous work of Bravi et al. has been demonstrated that CCM3 knock out cells exhibited a strong disorganisation of junctions, in particular of VE-cadherin clustering at cell membrane (Bravi et al., 2015).

To check the effect of Bmi1 on junctional organisation, both wild type and CCM3 knock out cells were treated with PTC209 with the same experimental conditions described before and subsequently analysed by immunofluorescence. In particular cells were stained for VE-cadherin and PECAM1 (FIG. 7).

Immunofluorescence analysis first confirmed that CCM3 knock out cells showed a strong disorganisation of junction compared to wild type. Indeed, VE-cadherin and PECAM1, as observed in FIG. 7 were lost from cell-cell contacts in CCM3 knock out cells.

PTC209 treatment anyway did not rescue junctional disorganisation in CCM3 knock out cells but also did not disturb junction organisation in wild type cells. These results suggested that PTC-209 per se did not perturb junctional organization in wild type conditions, but also that it was not sufficient to rescue the junction disorganization induced by Ccm3 loss.

Western blot and real time analysis of VE-cadherin were performed in parallel to confirm the reduction of VE-cadherin observed by immunofluorescence (FIG. 8A-C). VE-cadherin protein and transcript levels, as expected, were reduced in CCM3 knock out cells compare to wild type, as already shown (Bravi et al., 2015). It was confirmed also that PTC209 treatment did not rescue both VE-cadherin protein and transcript levels in CCM3 knock out.

These results, together with immunofluorescence analysis suggested that Bmi1 inhibition was not able to rescue VE-cadherin levels, and did not induce reorganisation of VE-cadherin or PECAM1 at cell-cell contact in CCM3 knock out cells.

Example 4: Bmi1 Inhibition Reduced EndMT Markers in CCM1 Knockout Cells

To test the effect of Bmi1 inhibition in another model, the inventors repeated the same experiment with PTC209 on immortalized lung endothelial cells wild type and knock out for CCM1. CCM1 knock out cells, as well as CCM3 knock out cells, derived from VECPAC/CCM1$^{fl/fl}$ mice. Once isolated CCM1$^{fl/fl}$ endothelial cells were immortalized and treated with TAT-Cre recombinase to induce Ccm1 gene deletion or were not treated and used as control.

Treatment with PTC209 was performed with the same experimental conditions used for CCM3 model. After treatment cells were analysed by western blot (FIG. 9), real time (FIG. 10) and immunofluorescence (FIG. 11) analysis. As previously reported (Maddaluno et al., 2013) (Cuttano et al., 2015) CCM1 knock out cells showed upregulation of EndMT markers both at protein and transcript levels (FIGS. 9A-B and FIG. 10). Interestingly this upregulation was milder when compared to upregulation observed in CCM3 model (FIG. 4A-B). This observation resembled what was previously observed for human patients as well as for CCM3 mouse model, namely that mutation in Ccm3 led to a more severe phenotype, with higher risk of cerebral haemorrhage and more severe malformations, compare to patients with mutation in Ccm1 and Ccm2 (Denier et al., 2006). Also on CCM1 knock out cells, as well as on CCM3 knock out cells, when treated with PTC209 a strong inhibition of EndMT markers was observed, both at protein and transcript levels. Again, as observed in CCM3, Klf4 was not downregulated in physiological condition (wild type), suggesting the same mechanism of regulation hypothesized for CCM3.

Results were confirmed also by immunofluorescence analysis (FIG. 11A). Indeed quantification of the relative fluorescence intensity (FIG. 11B) showed upregulation of Klf4, Sca1 and Fsp1 in CCM1 knockout cells compared to wild type cells and moreover that this upregulation was inhibited upon PTC209 treatment.

Example 5: Bmi1 Inhibition Rescued Junctional Disorganisation in CCM1 Knockout Endothelial Cells Also for CCM1 model, the inventors tested the effect of Bmi1 inhibition on junction organisation. The inventors repeated PTC209-treatment on CCM1 model with the same experimental conditions described before, and the inventors analysed VE-cadherin and PECAM1 expression by immunofluorescence analysis (FIG. 12) in parallel with real time analysis (FIG. 13).

First, results showed disorganisation at the level of junctions in CCM1 knock out cells compared to wild type cells (FIG. 12), as already published (Maddaluno et al., 2013). Then, upon Bmi1 inhibition with PTC209, wild type cells remained unchanged, while CCM1 knock out cells showed a visible reorganisation of junctions.

Real time analysis showed reduction of gene expression levels of PECAM1 in CCM1 knocks out cells compare to wild type, but not of VE-cadherin (FIG. 13). Moreover, despite the rescue of disorganisation of VE-cadherin and PECAM1 in CCM1 knock out cells treated with PTC209 observed in immunofluorescence analysis (FIG. 12), gene expression analysis did not show any rescue at the transcript levels. These results suggested that inhibition of Bmi1 induced reorganisation/clustering of VE-cadherin and PECAM1, which were already present in the cells, but not their de novo transcription and synthesis.

Comparing these results with results obtained on CCM3 (FIGS. 7 and 8), it was possible to confirm the hypothesis that Bmi1 inhibition rescued CCM1 but not CCM3 junctional disorganisation probably due to the more severe phenotype observed in CCM3 knock out cells.

Example 6: Ezh1/2 Inhibition Reduced EndMT Markers in CCM3 Knockout Cells

Starting from evidences in which PRC1 complex inhibition led to downregulation of EndMT markers in CCM3 and CCM1 knock out cells, the inventors also tested the effect of inhibition of PRC2 complex. To inhibit PRC2 complex, the inventors targeted Ezh2 and his partner Ezh 1, the core subunits of PRC2, with a specific inhibitor called UNC1999. UNC1999 blocked the Hystone-methyl transferase activity of PRC2 (Konze et al., 2013).

To perform these experiments, immortalized lung endothelial cells both wild type and CCM3 knock out were treated, with the same experimental strategy used for PTC209, with UNC1999 for 72 hours and subsequently lysed for western blot and real time analysis. UNC1999 was used in its specific optimal concentration, which was different to PTC209. As control DMSO was given to the cells in a volume equal to the volume of DMSO in which UNC1999 was previously dissolved to rich the optimal concentration.

Western blot (FIGS. 14A-B) and real time (FIG. 15) analysis showed the same upregulation of EndMT markers in CCM3 knock out cells respect to wild type cells, as observed in experiment with PTC209. Again, as shown before, Sca1 was not upregulated in CCM3 knock out cells at the transcript level.

Interestingly, also inhibition of PRC2, by blocking Ezh1/2 with UNC1999, led to downregulation of EndMT protein and gene expressions in CCM3 knock out cells, even if the downregulation was not as strong as the downregulation observed upon administration of PTC209.

Klf4 was still not influenced, as observed with PTC209, by the treatment in physiological condition (wild type), confirming the existence of a different mechanism of regulation in physiological condition compared to pathological one.

Example 7: Combined PRC1 and PRC2 Inhibition Reduced EndMT Markers in CCM3 KO Cells The inventors then tested the effect of the combined inhibition of PRC1 and PRC2 complexes.

It has indeed demonstrated that PRC1 and PRC2 can synergistically cooperate to regulate a number of developmental processes both in physiological and pathological conditions, such as cancer (Wang et al., 2015).

To evaluate whether a synergic cooperation, in regulating EndMT markers expression, between PRC1 and PRC2 existed, the inventors treated wild type and CCM3 knock out cells with a combination of PTC209 and UNC1999.

Briefly, wild type and CCM3 knock out cells were treated with either PTC209, UNC1999 or a combination of the two. PTC209 and UNC1999 were administrated at the same concentration used for the single treatment and DMSO was given as control in a volume equal to the sum of volumes of DMSO in which UNC1999 and PTC209 were previously dissolved.

Western blot analysis (FIGS. 16A and B) showed inhibition of the upregulation of EndMT markers observed in CCM3 knock out cells, upon administration of both PTC209 and UNC1999 alone and combination of the two drugs. Interestingly, combined inhibition of PRC1 and PRC2 reduced EndMT protein expression more than individual inhibition (FIG. 16B).

In parallel the same experiment was analysed by real time analysis (FIG. 17). Downregulation of EndMT markers upon drugs administration were confirmed also at transcript levels. It was again evident how PTC209 and UNC1999 synergistically cooperated to inhibit Klf4, Fsp1 and Sca1 upregulation in CCM3 knock out cells. With the same experimental conditions, cells were also analysed by immunofluorescence analysis (FIGS. 18A and B). Cells were thus stained for Klf4, Sca1 and Fsp1 after treatment with PTC209 and UNC199 alone and after treatment with the combination of the two drugs.

What was observed, in addition to the upregulation of EndMT markers in CCM3 knock out cells compared to wild type, was that combined treatment reduced EndMT markers fluorescence intensity more than single treatment.

Taken together western blot, real time and immunofluorescence analysis, it was evident that a synergistic cooperation between PRC1 and PRC2 existed, and that their combined inhibition was more efficient in reducing upregulation of EndMT markers in CCM3 knock out cells, compare to single drugs administration.

Example 8: Combined PRC1 and PRC2 Inhibition Rescued Junctional Disorganization in CCM3 Knock Out Cells The inventors then checked the effect of combined PRC1 and PRC2 inhibition on organisation of junctions in CCM3 in vitro model.

Experiment with combined PTC209 and UNC1999 treatments was repeated with the same experimental conditions described before and junction organisation was analysed through VE-cadherin staining and protein expression analysis (FIG. 19).

By representative immunostaining of VE-cadherin, it was evident the strong disorganisation of junctions in CCM3 knock out cells compare to wild type, as previously reported in literature (Bravi et al., 2015) and confirmed by the inventors' results (FIG. 7) and moreover it was shown a partially improvement of junction organisation upon combined treatment of PTC209 and UNC1999, differently to what was observed upon single administration (FIG. 19). Also under these condition wild type cells were not affected by combined treatment (FIG. 19).

Protein expression analysis, despite improvement observed by immunofluorescence analysis, did not show any rescue of VE-cadherin protein expression level upon combined administration of PTC209 and UNC1999 or single administration (FIG. 20), as observed previously in CCM1 and CCM3 in vitro models (FIG. 7 and FIG. 12). As explained before, a possible reason lied in the fact that VE-cadherin, upon combined treatment, was not de novo synthetized, but was reorganized/clustered at cell-cell contacts.

Example 9: Combined PRC1 and PRC2 Inhibition Reduced EndMT Markers in CCM1 KO Cells To evaluate the inhibitory effect of PTC209 combined with UNC1999 on EndMT markers observed in CCM3 knock out cells, on another model, the inventors repeated the same experiment on CCM1 in vitro model.

The inventors treated CCM1 knock out cells with PTC209 alone, UNC1999 alone and the combination of PTC209 and UNC1999 for 72 hours, as for CCM3 model. Again, DMSO was used as control in a volume equal to the sum of volumes of DMSO in which UNC1999 and PTC209 were previously dissolved.

Cells were subsequently lysed for western blot (FIG. 21) and real time analysis (FIG. 22).

By western blot analysis it was observed a reduction of EndMT markers upregulation observed in CCM1 knock out cells, upon treatment with PTC209 combined with UNC1999, but this inhibition was not consistent when compared to inhibition obtained with only PTC209 (FIGS. 21A and B).

Also by real time analysis, Sca1 and Fsp1 were downregulated in CCM1 knock out cells upon combined treatment in the same way as PTC209 treatment (FIG. 22). Klf4, in contrast, seems to be not downregulated upon PTC209 and UNC1999 combined treatment but only with PTC209 (FIG. 22).

Together with previous results obtained with inhibition of only Bmi1 on CCM1 model (FIGS. 9 to 13), it was possible to hypothesized that in CCM1 PRC1 and PRC2 did not cooperate to regulate EndMT markers expression, and that probably Bmi1 was more critical in the regulation compared to Ezh1/2.

Example 10: Inhibition of PRC1 and PRC2 Reduced Size and Number of Lesions in CCM3 KO Mice In order to translate the results described above, in which contemporary inhibition of PRC complexes in CCM3 knock out cells reduced EndMT markers expression, into a therapeutic opportunities, the inventors tested the effect of PTC209 and UNC1999 in vivo, on VECPAC/CCM3$^{fl/fl}$ mice.

In particular, VECPAC/CCM3$^{fl/fl}$ mice, were injected the first day after birth with 100 ug of tamoxifen to induce recombination of Ccm3 floxed-gene. Starting from the day after tamoxifen injection CCM3 knock out mice received daily an intragastric injection of PTC209 (10 ug/g body weight) combined with UNC1999 (25 ug/g body weight), and then were sacrificed eight days after birth for analysis. The two drugs were first dissolved in DMSO and then in 50 µL of corn oil. For this reason, half litter was treated with DMSO dissolved in oil as well, as control.

The brains of animals were analysed for size and number of lesions developed. Isolectin staining was used to visualize the brain vasculature in order to make the identification of lesions simpler.

Once stained brain sections were examined under confocal microscopy and the total number of lesions was calculated by summing all types of lesions per brain.

Pictures of the entire brains showed how treatment with PTC209 plus UNC1999 macroscopically reduced lesions in CCM3 knock out mice (FIG. 23A).

Furthermore, Isolectin staining on brain sections allowed a more precise calculation of the number of lesions and the amount of the total lesioned area. As shown in FIGS. 24A and 24B, the total lesioned area in parallel with the number of lesions per mm$^2$ of the brain area was strongly reduced in CCM3 knock out mice upon drugs treatment.

Interestingly, combined treatment reduced number of large lesions more than number of small lesions (FIG. 24C), suggestion that PRC complexes inhibition acted on lesion development and maintenance rather than on formation of new lesions.

These results demonstrated the promising possibility to use Bmi1 and Ezh1/2 as targets for a pharmacological therapy, to reduce the number and the size of formed lesions in genetic CCM patients.

Example 11: PRC1 Regulates EndMT Through β-Catenin Pathway

To understand the molecular mechanism though which PRC1 regulated EndMT markers expression, real-time PCR analysis were done on target genes of the three principal pathways that have been shown to be involved in EndMT and CCM development: Delta-Notch, TGFβ and β-catenin signalling pathway (Maddaluno et al., 2013) (Bravi et al., 2015). To perform these experiments, wild type and CCM3 knock out cells were treated with PTC209 with the same experimental conditions described before, and subsequently lysed for gene expression analysis.

Axin2 was checked as evidence of β-catenin pathway activation (FIG. 25A), Serpin1 and Id1 for TGFβ signalling (FIG. 25B), while Hes1 and Dll4 for Notch pathway activation (FIG. 25C).

Real time analysis (FIG. 25), showed upregulation of Axin2 (FIG. 25A), Serpin1 (FIG. 25B) and Id1 (FIG. 25B) in CCM3 knock out cells compared to wild type. These results suggested that β-catenin and TGFβ pathways were upregulated upon Ccm3 gene depletion thus were involved in EndMT phenotype, as already published (Maddaluno et al., 2013) (Bravi et al., 2015). Interestingly Bmi1 inhibition led to downregulation of Axin2 (FIG. 25A) and Id1 (FIG. 25B) both in physiological and pathological conditions suggesting that β-catenin and TGFβ pathways were regulated by PRC1 complex. Also Hes1 (FIG. 25C) was downregulated in pathological conditions while Serpin1 was upregulated (FIG. 25B).

The inventors started to analysed interaction between Bmi1 and β-catenin pathway. By immunofluorescence analysis on wild type and CCM3 knock out cells treated with PTC209 and DMSO as control, as already mentioned, the inventors checked expression of LEF1, a transcription factor that is directly activated by β-catenin and is responsible for transcriptional activation of Axin2 (Behrens et al., 1996), to see whether Bmi1 inhibition interfered with β-catenin pathway activation.

As shown in FIG. 26, LEF1 was upregulated in CCM3 knock out compare to wild type, reflecting the upregulation of Axin2 observed in real time analysis (FIG. 25A). Moreover, upon Bmi1 inhibition LEF1 was reduced in CCM3 knock cells (FIG. 26), confirming also by immunofluorescence analysis that PRC1 was involved in regulation of β-catenin activity. Once demonstrated the involvement of PRC1 in regulation β-catenin activity, the inventors analysed specifically the interaction between Bmi1 and β-catenin pathway, independently from CCM genes depletion, in order to simplify the system. The strategy adopted to understand the molecular mechanism trough which PRC1 complex regulated β-catenin was to individually stimulated β-catenin transcriptional activity in wild type cells, to check whether Bmi1 inhibition, independently from CCM genes depletion, was still able to reduced EndMT markers expression. Has been indeed already demonstrated that stimulation of β-catenin transcriptional activity, but not the stimulation of Wnt receptor though soluble Wnt, was able to induce EndMT markers upregulation in wild type cells (Bravi et al., 2015).

To induce β-catenin transcriptional activation, a constitutively active mutant called LefΔN-β-catΔC was used (Vleminckx, Kemler, & Hecht, 1999). LefΔN-β-catΔC was made by the fusion of the C-terminal part of the transcription factor LEF1 (able to bind the DNA) and the transactivation domain of the β-catenin. The derived protein was able to bind the DNA and constitutively activate β-catenin target genes, without playing any role at the membrane (Vleminckx et al., 1999).

Once produced the lentivirus expressing LefΔN-β-catΔC, wild type cells were infected the day after seeding with different microliters of viruses (5 uL, 20 uL and 40 uL). In parallel wild type cells were infected also with a lentivirus expressing GFP as control, to verify that there were no problems linked to technical methods.

To check whether the plasmid containing LefΔN-β-catΔC, and GFP as control, were correctly expressed, infected wild type cells were lysated six days after infection for western blot and gene expression analysis. HA-tag, a sequence present in LefΔN-β-catΔC final product, and GFP was checked with western blot analysis (FIG. 27A), while Axin2 (direct target of active β-catenin) was checked in gene expression analysis (FIG. 27B). Wild type cells reacted to infection in a dose dependent manner, and the expression of LefΔN-β-catΔC led to strong activation of Axin2 in cells infected with 40 μL of lentivirus (FIG. 27B).

Based on these results, infection with the same experimental condition was repeated on wild type cells, the day after seeding with 40 ul of the concentrated lentivirus expressing LefΔN-β-catΔC and GFP as control. Nine days after infection cells were treated with PTC209 for other 72 hours and subsequently lysed for gene expression analysis (FIG. 28). Real time analysis showed upregulation of Sca1 and Fsp1 upon infection with LefΔN-β-catΔC-lentivirus, confirming what has been previously reported, namely β-catenin transcriptional activity stimulation was able to induce stem-cell/EndMT markers (Bravi et al., 2015). Klf4 was not upregulated probably due to different timing of stimulation used by Bravi et al.

Remarkably, upon Bmi1 inhibition, Sca1 and Fsp1 upregulation was strongly reduced (FIG. 28). This suggested that PRC1 complex, independently from CCM genes depletion, participated in the regulation of EndMT markers expression.

REFERENCES

Akers, A. L., et al., (2009) *Human Molecular Genetics*, 18 (5), 919-30.
Bäumer, S., et al. (2006). *Blood*, 107 (12), 4754-62.
Bazzoni, G. (2004). *Physiological Reviews*, 84 (3), 869-901.
Behrens, J., et al., (1996) *Nature*, 382 (6592), 638-642.
Bessman, M. J., et al., (2016) *Journal of Biological Chemistry*, 5, e17600.
Birbrair, A., et al., (2015) *Clinical Science*, 128 (2), 81-93.
Boulday, G., et al., (2009) *Disease Models & Mechanisms*, 2 (3-4), 168-77.
Bourdeau, A., et al., (1999) *The Journal of Clinical Investigation*, 104 (10), 1343-51.
Bravi, L., et al., (2016) *Stroke*, 47 (3), 886-890.
Bravi, L., et al., (2015) *PNAS*, 112 (27), 8421-6.
Bunker, C. A., et al., (1994) *Mol Cell Biol*, 14 (3), 1721-1732.
Butz, S., et al., (1992) *Science* (New York, N.Y.), 257 (5073), 1142-4.
Cai, Y., et al., (2015). *Diagnostic Pathology*, 10 (1), 35.
Carman, C. V., et al., (2007) *Immunity*, 26 (6), 784-797.
Carmeliet, P., et al., (2000) *Nature*, 407 (6801), 249-257.
Ceccarelli, D. F., et al., (2011) *The Journal of Biological Chemistry*, 286 (28), 25056-64.
Cho, J.-H., et al., (2013) *The Journal of Biological Chemistry*, 288 (5), 3406-18.
Choquet, H., et al., (2015) *Journal of Neurosurgical Sciences*, 59 (3), 211-20.
Corada, M., et al., (2010) *Developmental Cell*, 18 (6), 938-949.
Correia, A. C. P., et al., *Journal of Cell Science*, 129 (3), 569-579.
Crosby, C. V., et al., (2005) *Blood*, 105 (7), 2771-6.
Crose, L. E. S., et al., (2009) *Journal of Biological Chemistry*, 284 (20), 13301-13305.
Cuttano, R., et al., (2015) *EMBO Molecular Medicine*, 8 (1), 1-19.
de Kreuk, B. J., et al., (2016) *eLife*, 5 (JANUARY2016), 1-23.
Dejana, E. (2004) *Nature Reviews Molecular Cell Biology*, 5 (4), 261-270.
Dejana, E., et al., (2017) *Nature Communications*, 8, 14361.
Dejana, E., et al., (2013) *Journal of Cell Science*, 126 (12), 2545-2549.
Dejana, E., et al., (2008) *Journal of Cell Science*, 121 (13), 2115-2122.
Dejana, E., et al., (2009a) *Developmental Cell*, 16 (2), 209-221.
Dejana, E., T et al., (2009b) *Developmental Cell*, 16 (2), 209-221.
Dejana, E., et al., (2009c) *Developmental Cell*, 16 (2), 209-221.
Denier, C., et al., (2006) *Annals of Neurology*, 60 (5), 550-6.
Dimri, G. P. (2008) *Cancer*, 67 (11), 5083-5089.
Draheim, K. M., et al., (2014) *Journal of Cell Science*, 127 (4), 701-707.
Dubovsky, J., et al., (1995) *Human Molecular Genetics*, 4 (3), 453-8.
Durand, M. J., et al., (2013) *Microcirculation*, 20 (3), 239-247.
Dyrna, F., et al., (2013) *Journal of Neuroimmune Pharmacology*, 8 (4), 763-773.
El-Karim, E. A., et al., (2013) *Molecular Cancer*, 12 (1), 89.
Fischer, A., et al., (2013) *Trends in Molecular Medicine*, 19 (5), 302-308.
Furuse, M., et al., (2006) *Trends in Cell Biology*, 16 (4), 181-188.
Gault, J., et al., (2005) *Stroke*, 36 (4), 872-4.
Gavard, J., et al., (2006) *Nature Cell Biology*, 8 (11), 1223-1234.
Giampietro, C., et al., (2012) *Blood*, 119 (1528-0020 (Electronic)), 2159-2170.
Glading, A., et al., (2007) *The Journal of Cell Biology*, 179 (2), 247-54.
Glinsky, G. V, et al., (2005) *J Clin Invest*. 115 (6), 1503-1521.
Gunel, M., et al., (2002) *PNAS*, 99 (16), 10677-82.
Guo, W., et al., (2007) *Cancer Res*. (11), 5083-5090.
Guo, Y., et al., (2015) *Molecular Cancer Therapeutics*, 14 (10), 2215-27.
Hämmerling, B., et al., (2006) *Cell and Tissue Research*, 324 (1), 55-67.
Hansen, K. H., et al., (2008) *Nature Cell Biology*, 10 (11), 1291-1300.
Harel, L., et al., (2009) *Neuron*, 63 (5), 585-591.
Hartsock, A., et al., (2008) *Biochim Biophys Acta*, 1778 (3), 660-669.
He, Y., et al., (2010) *Science Signaling*, 3 (116), ra26.
Hilder, T. L., et al., (2007) *Journal of Proteome Research*, 6 (11), 4343-4355.
Hu, R., et al., (2011) *Gut and Liver*, 5 (2), 154-9.
Hwang, J., et al., (2014) *The Int. J. of Biochem. & Cell Biol.*, 47 (December 2013), 118-148.
Ichise, T., et al., (2014) *Journal of Cell Science*, 127 (4), 845-857.
Jacobs, J. L., et al., (1999) *Genes {&} Development*, 2678-2690.
Knudson, A. G. (1971) *PNAS*, 68 (4), 820-3.
Komiya, Y., et al., (2008) *Organogenesis*, 4 (2), 68-75.
Konze, K. D., et al., (2013) *ACS Chemical Biology*, 8 (6), 1324-1334.
Kreso, A., et al., (2013) *Nature Medicine*, 20 (1), 29-36.
Kumarswamy, R., et al., (2012) *Arteriosclerosis, Thrombosis, and Vasc. Biol.*, 32 (2), 361-369.
Ismail I H, et al., (2013) *J Biol Chem*. 288 (37): 26944-54.
Lampugnani, M. G., et al., (1997) *Journal of Cell Science*, 110 (Pt 17), 2065-77.
Lampugnani, M. G., et al., (2017) *Current Opinion in Hematology*, 24 (3), 1.
Lampugnani, M. G., et al., (2006) *Journal of Cell Biology*, 174 (4), 593-604.

Lampugnani, M. G., et al., (2010a) *Journal of Cell Science*, 123 (7), 1073-1080.
Lampugnani, M. G., et al., (2010b) *Journal of Cell Science*, 123 (7), 1073-1080.
Lesca, G., (2006) *Human Mutation*, 27 (6), 598-598.
Levine, S. S., et al., (2004) *Trends in Biochemical Sciences*, 29 (9), 478-485.
Liebner, S., et al., (2004) *Journal of Cell Biology*, 166 (3), 359-367.
Lien, W. H., et al., (2014) *Genes and Development*, 28 (14), 1517-1532.
Limaye, N., et al., (2009) *Human Molecular Genetics*, 18 (R1), R65-74.
Liu, W., et al., (2013) *Molecular Cell*, 49 (4), 719-729.
Livet, J., et al., (2007) *Nature*, 450 (7166), 56-62.
Lopez, D., et al., (2009) *Archives of Biochemistry and Biophysics*, 482 (1-2), 77-82.
Maddaluno, L., et al., (2013) *Nature*, 498 (7455), 492-496.
Margueron, R., et al., (2009) *Nature*, 461 (7265), 762-767.
Mariotti, A., et al., (2007) *Expert Opinion on Investigational Drugs*, 16 (4), 451-465.
McDonald, D. A., et al., (2011) *Human Molecular Genetics*, 20 (2), 211-222.
Medici, D., et al., (2012) *Seminars in Cancer Biology*, 22 (5-6), 379-384.
Murakami, M., et al., (2009) *Journal of Clinical Investigation*, 119 (7), 2113.
Navarro, P., et al., (1998) *The Journal of Cell Biology*, 140 (6), 1475-84.
Y Nishida, et al., (2017) *Blood Cancer Journal*, 7, e527.
Oguro, H., et al., (2010) *Cell Stem Cell*, 6 (3), 279-286.
Paranjape, A. et al., (2014) *BMC Cancer*, 14 (1), 785.
Park, I.-K., et al., (2004) *The Journal of Clinical Investigation*, 113 (2), 175-9.
Park, I., (2003) *Nature*, 423 (6937), 302-305.
Radulović, V., et al., (2013) *Leukemia*, 27 (3), 523-533.
Rajendran, P., et al., (2013) *International Journal of Biological Sciences*, 9 (10), 1057-1069.
Revencu, N., et al., (2008) *Human Mutation*, 29 (7), 959-965.
Riant, F., et al., (2010) *FEBS Journal*, 277 (5), 1070-1075.
Rigamonti, D., et al., (1988a) *New England Journal of Medicine*, 319 (6), 343-347.
Rigamonti, D., et al., (1988b) *New England Journal of Medicine*, 319 (6), 343-347.
Risau, W., et al., (2000) *Morphogenesis of endothelium*.
Rizo, A., et al., (2009) *Blood*, 114 (8), 1498-1505.
Rudini, N., et al., (2008) *The EMBO Journal*, 27 (7), 993-1004.
Serebriiskii, I., et al., (1997) *Oncogene*, 15 (9), 1043-9.
Siddique, H. R., et al., (2013) *PLOS ONE*, 8 (5).
Speck, O., et al., (2003) *Nature*, 421 (6918), 83-87.
Stockton, R. A., et al., (2010) *The Journal of Experimental Medicine*, 207 (4), 881-896.
Taddei, A., et al., (2008) *Nature Cell Biology*, 10 (8), 923-934.
Tavares, L., et al., (2012) *Cell*, 148 (4), 664-678.
Tournier-Lasserve, E. (2007) *Neuro-Chirurgie*, 53 (2-3 Pt 2), 136-40.
Turner, J. R., et al., (2014) *Seminars in Cell & Developmental Biology*, 36, 204-12.
van Kemenade, et al., (2001) *Blood*, 97 (12), 3896-901. R
van Lohuizen, M., et al., (1991) *Cell*, 65 (5), 737-52.
Velichutina, I., et al., (2010) *Blood*, 116 (24), 5247-5255.
Vleminckx, K., et al., (1999) *Mechanisms of Development*, 81 (1-2), 65-74.
Wallez, Y., et al., (2008) *Biochimica et Biophysica Acta-Biomembranes*, 1778 (3), 794-809.
Wang, G. G., et al., (2015) *Blood*, 125 (8), 1217-25.
Wang, W., et al., (2015) *Medicinal Research Reviews*, 35 (6), 1220-1267.
Weber, C., et al., (2007) *Nature Reviews Immunology*, 7 (6), 467-477.
Whitehead, K. J., et al., (2009) *Nature Medicine*, 15 (2), 177-184.
Wildenberg, G. A., et al., (2006) *Cell*, 127 (5), 1027-1039.
Williams, E. J., et al., (2001) *The Journal of Biological Chemistry*, 276 (47), 43879-86.
Yamada, S., et al., (2005) *Cell*, 123 (5), 889-901.
Zegers, M. M., et al., (2014) *Small GTPases*, 5, e28997.
Zhan, T., et al., (2017) *Oncogene*, 36 (11), 1461-1473.
Zhou, H. J., et al., (2016) *Nature Medicine*, 22 (9), 1033-1042.
Zhou, Z., et al., (2016). *Nature*, 532 (7597).

The invention claimed is:

1. A method for the treatment of an endothelial to mesenchymal transition associated pathology in a patient in need thereof, the method consisting of administering an effective amount of an inhibitor of polycomb to the patient; wherein the inhibitor is:

PTC-596 (5-fluoro-2-(6-fluoro-2-methyl-1H-benzo[d]imidazol-1-yl)-N4-(4-(trifluoromethyl)phenyl)pyrimidine-4,6-diamine hydrochloride) or a pharmaceutically acceptable salt thereof; or a combination of PTC-596 or a pharmaceutically acceptable salt thereof and PTC-209 (N-(2,6-dibromo-4-methoxyphenyl)-4-(2-methylimidazo[1,2-a]pyrimidin-3-yl) thiazol-2-amine) or a pharmaceutically acceptable salt thereof; or a combination of PTC-596 or a pharmaceutically acceptable salt thereof and UNC-1999 (N-[(6-methyl-2-oxo-4-propyl-1H-pyridin-3-yl)methyl]-1-propan-2-yl-6-[6-(4-propan-2-ylpiperazin-1-yl) pyridin-3-yl]indazole-4-carboxamide) or a pharmaceutically acceptable salt thereof; and wherein the endothelial to mesenchymal transition associated pathology is selected from the group consisting of: cerebral cavernous malformation (CCM), atherosclerosis, transplant arteriopathy, cardiac fibrosis, chronic obstructive pulmonary disease (COPD), pulmonary fibrosis, portal hypertension, heterotopic ossification systemic sclerosis, diabetic renal interstitial fibrosis, diabetes retinopathy, primary mielofibrosis, fibrodysplasia ossificans progressiva, and kidney fibrosis.

2. The method according to claim 1 wherein said inhibitor is an inhibitor of at least one polycomb Repressive Complex.

3. The method according to claim 2 wherein the polycomb Repressive Complex is PRC1 or PRC2.

4. The method according to claim 1 wherein the inhibitor is a combination of PTC-596 or a pharmaceutically acceptable salt thereof and PTC-209 or a pharmaceutically acceptable salt thereof; or a combination of PTC-596 or a pharmaceutically acceptable salt thereof and UNC-1999 or a pharmaceutically acceptable salt thereof.

5. The method according to claim 1 wherein the endothelial to mesenchymal transition associated pathology is cerebral cavernous malformation.

6. The method according to claim 1, wherein the effective amount is about 600 mg and is administered between twice a week and once per month.

7. The method according to claim 1, wherein the effective amount is a dose between 0.001 to 200 mg/kg.

8. The method according to claim 7, wherein the dose is 0.2-100 mg/kg.

9. The method according to claim 8, wherein the dose is 0.2-50 mg/kg.

10. The method according to claim 9, wherein the dose is 0.2-20 mg/kg.

11. The method according to claim 10, wherein the dose is 0.2-10 mg/kg.

12. The method according to claim 11, wherein the dose is 0.2-7 mg/kg.

13. The method according to claim 12, wherein the dose is 0.2-5 mg/kg.

* * * * *